United States Patent
Anderson et al.

(10) Patent No.: US 9,717,580 B2
(45) Date of Patent: Aug. 1, 2017

(54) PELVIC FLOOR IMPLANT SYSTEM AND METHOD OF ASSEMBLY

(75) Inventors: Kimberly A. Anderson, Eagan, MN (US); Robert E. Lund, St. Michael, MN (US); Mark S. Bouchier, Lakeville, MN (US); Francis D. Sturzl, III, Maplewood, MN (US); James A. Gohman, Plymouth, MN (US); Timothy A. Bachman, St. Paul, MN (US)

(73) Assignee: Astora Women's Health, LLC, Malvern, PA (US)

( * ) Notice: Subject to any disclaimer, the term of this patent is extended or adjusted under 35 U.S.C. 154(b) by 1061 days.

(21) Appl. No.: 11/755,422

(22) Filed: May 30, 2007

(65) Prior Publication Data

US 2007/0225546 A1  Sep. 27, 2007

Related U.S. Application Data

(63) Continuation of application No. 10/335,119, filed on Dec. 31, 2002, now Pat. No. 7,229,453, which is a
(Continued)

(51) Int. Cl.
*A61B 17/08* (2006.01)
*A61F 2/00* (2006.01)
(Continued)

(52) U.S. Cl.
CPC ........ *A61F 2/0045* (2013.01); *A61B 17/0401* (2013.01); *A61B 17/0487* (2013.01);
(Continued)

(58) Field of Classification Search
CPC ............ A61B 17/0401; A61B 17/0469; A61B 17/0482; A61B 17/0487; A61B 17/06004;
(Continued)

(56) References Cited

U.S. PATENT DOCUMENTS 2,738,790 A   3/1956 Todt et al.
3,124,136 A   3/1964 Usher
(Continued)

FOREIGN PATENT DOCUMENTS

DE   2305815   2/1973
DE   4220283 C2   5/1994
(Continued)

OTHER PUBLICATIONS

Albert H. Aldridge. B.S., M.D., F.A.C.S., Transplantation of Fascia for Relief of Urinary Stress Incontinence, American Journal of Obstetrics and Gynecology, V. 44, pp. 398-411, (1948).
(Continued)

*Primary Examiner* — Julian W Woo
(74) *Attorney, Agent, or Firm* — Skaar Ulbrich Macari, P.A.

(57) ABSTRACT

Surgical articles, implants and components suitable creating composite slings are described. Novel procedures for assembling and utilizing composite slings are also detailed.

14 Claims, 16 Drawing Sheets

Related U.S. Application Data continuation-in-part of application No. 10/106,086, filed on Mar. 25, 2002, now abandoned, and a continuation-in-part of application No. 10/280,945, filed on Oct. 25, 2002, now Pat. No. 7,048,682, which is a continuation of application No. 09/917,445, filed on Jul. 27, 2001, now Pat. No. 6,802,807, which is a continuation of application No. 10/005,837, filed on Nov. 9, 2001, now abandoned, said application No. 10/335,119 is a continuation-in-part of application No. 10/306,179, filed on Nov. 27, 2002, now Pat. No. 7,070,556.

(60) Provisional application No. 60/263,472, filed on Jan. 23, 2001, provisional application No. 60/269,829, filed on Feb. 20, 2001, provisional application No. 60/279,794, filed on Mar. 29, 2001, provisional application No. 60/281,350, filed on Apr. 4, 2001, provisional application No. 60/295,068, filed on Jun. 1, 2001, provisional application No. 60/302,929, filed on Jul. 3, 2001, provisional application No. 60/306,915, filed on Jul. 20, 2001, provisional application No. 60/307,836, filed on Jul. 25, 2001, provisional application No. 60/405,139, filed on Aug. 22, 2002.

(51) Int. Cl.
  *A61B 17/04* (2006.01)
  *A61B 17/06* (2006.01)
  *A61B 17/062* (2006.01)
  *A61B 17/30* (2006.01)
  *A61B 17/3211* (2006.01)
  *A61B 17/00* (2006.01)
  *A61B 90/00* (2016.01)
  *A61B 50/30* (2016.01)

(52) U.S. Cl.
  CPC ...... *A61B 17/062* (2013.01); *A61B 17/06004* (2013.01); *A61B 17/06109* (2013.01); *A61B 17/0469* (2013.01); *A61B 17/0482* (2013.01); *A61B 17/06066* (2013.01); *A61B 17/30* (2013.01); *A61B 17/3211* (2013.01); *A61B 50/30* (2016.02); *A61B 90/02* (2016.02); *A61B 2017/00805* (2013.01); *A61B 2017/06009* (2013.01); *A61B 2017/06042* (2013.01); *A61B 2017/06085* (2013.01)

(58) Field of Classification Search
  CPC ........ A61B 17/06066; A61B 17/06109; A61B 17/062; A61B 17/30; A61B 17/3211; A61B 19/026; A61B 19/24; A61B 2017/00805; A61B 2017/06009; A61B 2017/06042; A61B 2017/0608
  USPC ..... 606/151, 228; 424/422–424; 600/30, 37; 602/47, 48; 623/13.11
  See application file for complete search history.

(56) References Cited

U.S. PATENT DOCUMENTS

| | | |
|---|---|---|
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,513,848 A * | 5/1970 | Garvey et al. ............... 606/228 |
| 3,545,008 A | 12/1970 | Bader, Jr. ................... 623/13.15 |
| 3,580,313 A | 5/1971 | McKnight |
| 3,763,860 A | 10/1973 | Clarke |
| 3,789,828 A | 2/1974 | Schulte |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,235,238 A | 11/1980 | Ogiu et al. |
| 4,246,660 A | 1/1981 | Wevers |
| 4,441,497 A | 4/1984 | Paudler |
| 4,509,516 A | 4/1985 | Richmond |
| 4,632,100 A | 12/1986 | Somers et al. |
| 4,769,038 A | 9/1988 | Bendavid et al. ............ 606/151 |
| 4,775,380 A | 10/1988 | Seedhom et al. |
| 4,857,041 A | 8/1989 | Annis et al. |
| 4,865,031 A | 9/1989 | O'Keeffe |
| 4,920,986 A | 5/1990 | Biswas |
| 4,932,962 A | 6/1990 | Yoon et al. |
| 4,938,760 A | 7/1990 | Burton et al. |
| 4,969,892 A | 11/1990 | Burton et al. |
| 4,979,956 A * | 12/1990 | Silvestrini ................ 623/13.11 |
| 5,007,894 A | 4/1991 | Enhorning |
| 5,012,822 A | 5/1991 | Schwarz |
| 5,013,292 A | 5/1991 | Lemay |
| 5,019,032 A | 5/1991 | Robertson |
| 5,032,508 A | 7/1991 | Naughton et al. |
| 5,036,867 A | 8/1991 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,188,636 A | 2/1993 | Fedotov |
| 5,209,756 A | 5/1993 | Seedhom et al. |
| 5,250,033 A | 10/1993 | Evans et al. |
| 5,256,133 A | 10/1993 | Spitz |
| 5,281,237 A | 1/1994 | Gimpelson |
| 5,328,077 A | 7/1994 | Lou |
| 5,337,736 A | 8/1994 | Reddy |
| 5,362,294 A | 11/1994 | Seitzinger |
| 5,368,595 A | 11/1994 | Lewis |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,425,740 A | 6/1995 | Hutchinson, Jr. ............. 606/157 |
| 5,439,467 A | 8/1995 | Benderev et al. |
| 5,520,700 A | 5/1996 | Beyar et al. |
| 5,544,664 A | 8/1996 | Benderev et al. |
| 5,562,689 A | 10/1996 | Green et al. |
| 5,571,139 A | 11/1996 | Jenkins, Jr. |
| 5,591,163 A | 1/1997 | Thompson |
| 5,611,515 A | 3/1997 | Benderev et al. |
| 5,628,756 A | 5/1997 | Barker, Jr. et al. |
| 5,633,286 A | 5/1997 | Chen |
| 5,669,935 A | 9/1997 | Rosenman et al. |
| 5,683,349 A | 11/1997 | Makower et al. |
| 5,807,403 A | 9/1998 | Beyar et al. |
| 5,836,314 A | 11/1998 | Benderev et al. |
| 5,836,315 A | 11/1998 | Benderev et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,922,026 A | 7/1999 | Chin ............................ 606/151 |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A * | 9/1999 | Li ................................ 600/37 |
| 5,972,000 A | 10/1999 | Beyar et al. |
| 5,988,171 A | 11/1999 | Sohn et al. |
| 5,997,554 A | 12/1999 | Thompson |
| 6,010,447 A | 1/2000 | Kardjian |
| 6,030,393 A | 2/2000 | Corlew |
| 6,031,148 A | 2/2000 | Hayes et al. |
| 6,042,534 A | 3/2000 | Gellman et al. |
| 6,042,536 A * | 3/2000 | Tihon et al. .................. 600/37 |
| 6,050,937 A | 4/2000 | Benderev |
| 6,053,935 A | 4/2000 | Brenneman et al. |

(56) References Cited

U.S. PATENT DOCUMENTS

| | | | |
|---|---|---|---|
| 6,068,591 A | 5/2000 | Bruckner et al. | |
| 6,071,290 A | 6/2000 | Compton | |
| 6,106,545 A | 8/2000 | Egan | |
| 6,110,101 A | 8/2000 | Tihon et al. | |
| 6,117,067 A | 9/2000 | Gil-Vernet | |
| 6,168,611 B1 | 1/2001 | Rizvi | |
| 6,221,005 B1 | 4/2001 | Bruckner et al. | |
| 6,273,852 B1 | 8/2001 | Lehe et al. | |
| 6,302,840 B1 | 10/2001 | Benderev | |
| 6,306,079 B1 | 10/2001 | Trabucco | |
| 6,328,744 B1 | 12/2001 | Harari et al. | |
| 6,334,446 B1 | 1/2002 | Beyar | |
| 6,352,553 B1 | 3/2002 | van der Burg et al. | |
| 6,382,214 B1 | 5/2002 | Raz et al. | |
| 6,406,423 B1 | 6/2002 | Scetbon | |
| 6,406,480 B1 | 6/2002 | Beyar et al. | |
| 6,475,139 B1 | 11/2002 | Miller | |
| 6,478,727 B2 | 11/2002 | Scetbon | |
| 6,482,214 B1 * | 11/2002 | Sidor et al. | 606/151 |
| 6,494,906 B1 | 12/2002 | Owens | |
| 6,502,578 B2 | 1/2003 | Raz et al. | |
| 6,530,943 B1 | 3/2003 | Hoepffner et al. | |
| 6,582,443 B2 | 6/2003 | Cabak et al. | |
| 6,592,515 B2 * | 7/2003 | Thierfelder et al. | 600/37 |
| 6,702,827 B1 | 3/2004 | Lund et al. | 606/151 |
| 6,872,227 B2 | 3/2005 | Sump et al. | 606/151 |
| 7,621,864 B2 * | 11/2009 | Suslian et al. | 600/30 |
| 2001/0000533 A1 | 4/2001 | Kovac | |
| 2001/0049467 A1 | 12/2001 | Lehe et al. | |
| 2002/0022841 A1 | 2/2002 | Kovac | |
| 2002/0028980 A1 | 3/2002 | Thierfelder et al. | |
| 2002/0055748 A1 | 5/2002 | Gellman et al. | |
| 2002/0058959 A1 | 5/2002 | Gellman | |
| 2002/0068948 A1 | 6/2002 | Stormby et al. | |
| 2002/0072694 A1 | 6/2002 | Snitkin et al. | |
| 2002/0077526 A1 | 6/2002 | Kammerer et al. | |
| 2002/0091373 A1 | 7/2002 | Berger | |
| 2002/0099258 A1 | 7/2002 | Staskin et al. | |
| 2002/0099259 A1 | 7/2002 | Anderson et al. | |
| 2002/0099260 A1 | 7/2002 | Suslian et al. | |
| 2002/0107430 A1 | 8/2002 | Neisz et al. | |
| 2002/0107525 A1 | 8/2002 | Harari et al. | |
| 2002/0115906 A1 | 8/2002 | Miller | |
| 2002/0128670 A1 | 9/2002 | Ulmsten et al. | |
| 2002/0138025 A1 | 9/2002 | Gellman et al. | |
| 2002/0147382 A1 | 10/2002 | Neisz et al. | |
| 2002/0151762 A1 | 10/2002 | Rocheleau et al. | |
| 2002/0151909 A1 | 10/2002 | Gellman et al. | |
| 2002/0151910 A1 | 10/2002 | Gellman et al. | |
| 2002/0156487 A1 | 10/2002 | Gellman et al. | |
| 2002/0156488 A1 | 10/2002 | Gellman et al. | |
| 2002/0188169 A1 | 12/2002 | Kammerer et al. | |
| 2003/0004395 A1 | 1/2003 | Therin | |
| 2003/0009181 A1 | 1/2003 | Gellman et al. | |
| 2003/0023136 A1 | 1/2003 | Raz | |
| 2003/0023137 A1 | 1/2003 | Gellman | |
| 2003/0023138 A1 | 1/2003 | Luscombe | |
| 2003/0036676 A1 | 2/2003 | Scetbon | |
| 2003/0045774 A1 | 3/2003 | Staskin et al. | |
| 2003/0050530 A1 | 3/2003 | Neisz et al. | |
| 2003/0065402 A1 | 4/2003 | Anderson et al. | |

FOREIGN PATENT DOCUMENTS

| | | |
|---|---|---|
| EP | 0 470 308 A1 | 2/1992 |
| EP | 0 650 703 A1 | 6/1994 |
| EP | 0 643 945 A2 | 7/1994 |
| EP | 1 093 758 A1 | 4/2001 |
| SU | 1225547 A1 | 4/1986 |
| SU | 1342486 A | 10/1987 |
| WO | WO 93/17635 A1 | 9/1993 |
| WO | WO 93/19678 A2 | 10/1993 |
| WO | WO 98/19606 A1 | 5/1998 |
| WO | WO 98/35616 A1 | 8/1998 |
| WO | WO 98/35632 A1 | 8/1998 |
| WO | WO 99/52450 A1 | 10/1999 |
| WO | WO 00/64370 A1 | 2/2000 |
| WO | WO 00/13601 A1 | 3/2000 |
| WO | WO 00/18319 A1 | 4/2000 |
| WO | WO 00/57812 A1 | 10/2000 |
| WO | WO 00/74594 A1 | 12/2000 |
| WO | WO 00/74613 A1 | 12/2000 |
| WO | WO 00/74633 A2 | 12/2000 |
| WO | WO 01/26581 A1 | 4/2001 |
| WO | WO 01/39670 A1 | 6/2001 |
| WO | WO 01/45589 A1 | 6/2001 |
| WO | WO 01/56499 A1 | 8/2001 |
| WO | WO 02/28312 A1 | 4/2002 |
| WO | WO 02/30293 A | 4/2002 |
| WO | WO 02/32284 A2 | 4/2002 |
| WO | WO 02/34124 A2 | 5/2002 |
| WO | WO 02/39890 A2 | 5/2002 |
| WO | WO 02/058564 A | 8/2002 |
| WO | WO 02/071953 A2 | 9/2002 |
| WO | WO 02/078552 A1 | 10/2002 |

OTHER PUBLICATIONS

Araki, Tohru et al., The Loop-Loosening Procedure for Urination Difficulties After Stamey Suspension of the Vesical Neck, The Journal of Urology, vol. 144, pp. 319-323 (Aug. 1990).

Asmussen, M. et.al., Simultaneous Urethro-Cystometry With a New Technique, Scand J Urol Nephrol 10, p. 7-11 (1976).

Beck, Peter R. et al., Treatment of Urinary Stress Incontinence With Anterior Colporrhaphy, Obstetrics and Gynecology, vol. 59 (No. 3), pp. 269-274 (Mar. 1982).

Benderev, Theodore V., MD, A Modified Percutaneous Outpatient Bladder Neck Suspension System, Journal of Urology, vol. 152, pp. 2316-2320 (Dec. 1994).

Benderev, Theodore V., MD, Anchor Fixation and Other Modifications of Endoscopic Bladder Neck Suspension, Urology, vol. 40, No. 5, pp. 409-418 (Nov. 1992).

Bergman, Arieh et al., Three Surgical Procedures for Genuine Stress Incontinence: Five-Year Follow-Up of a Prospective Randomized Study, Am J Obstet Gynecol, vol. 173 No. 1, pp. 66-71 (Jul. 1995).

Blaivas, Jerry et al., Pubovaginal Fascial Sling for the Treatment of Complicated Stress Urinary Incontinence, The Journal of Urology, vol. 145, pp. 1214-1218 (Jun. 1991).

Blaivas, Jerry et al., Type III Stress Urinary Incontinence: Importance of Proper Diagnosis and Treatment, Surgical Forum, pp. 473-475, (1984).

Blavis, Jerry, Commentary: Pubovaginal Sling Procedure, Experience with Pubovaginal Slings, pp. 93-101 (1990).

Bryans, Fred E., Marlex Gauze Hammock Sling Operation With Cooper's Ligament Attachment in the Management of Recurrent Urinary Stress Incontinence, American Journal of Obstetrics and Gynecology, vol. 133, pp. 292-294, 1979.

Burch, John C., Urethrovaginal Fixation to Cooper's Ligament for Correction of Stress Incontinence, Cystocele, and Prolapse, Am. J. Obst. & Gyn, vol. 31, pp. 281-290 (1961).

Choe, Jong M. et al., Gore-Tex Patch Sling: 7 Years Later, Urology, vol. 54, pp. 641-646 (1999).

Cook/Ob Gyn®, Urogynecology, Copyright Cook Urological Inc., pp. 1-36 (1996).

Das, Sakti et al., Laparoscopic Colpo-Suspension, The Journal of Urology. vol. 154, pp. 1119-1121 (Sep. 1995).

Decter, Ross M., Use of the Fascial Sling for Neurogenic Incontinence: Lessons Learned, The Journal of Urology, vol. 150, pp. 683-686 (Aug. 1993).

DeLancey, John, MD, Structural Support of the Urethra as it Relates to Stress Urinary Incontinence: The Hammock Hypothesis, Am J Obstet Gynecol, vol. 170 No. 6, pp. 1713-1723 (Jun. 1994).

Enzelsberger, H. et al., Urodynamic and Radiologic Parameters Before and After Loop Surgery for Recurrent Urinary Stress Incontinence. Acta Obstet Gynecol Scand, 69, pp. 51-54 (1990).

Eriksen, Bjarne C. et al., Long-Term Effectiveness of the Burch Colposuspension in Female Urinary Stress Incontinence, Acta Obstet Gynecol Scand, 69. pp. 45-50 (1990).

(56) References Cited

OTHER PUBLICATIONS

Falconer, C. et al., Clinical Outcome and Changes in Connective Tissue Metabolism After Intravaginal Slingplasty in Stress Incontinence Women, International Urogynecology Journal, pp. 133-137 (1966).
Falconer, C. el al., Influence of Different Sling Materials of Connective Tissue Metabolism in Stress Urinary Incontinent Women, International Urogynecology Journal, Supp. 2, pp. S19-S23 (2001).
Gilja, Ivan et al., A Modified Raz Bladder Neck Suspension Operation (Transvaginal Burch), The Journal of Urology, vol. 153, pp. 1455-1457 (May 1995).
Gittes, Ruben F. et al., No-Incision Pubovaginal Suspension for Stress Incontinence, The Journal of Urology, vol. 138 (Sep. 1987).
Handa, Victoria L. et al, Banked Human Fascia Lata for the Suburethral Sling Procedure: A Preliminary Report, Obstetrics & Gynecology, vol. 88 No. 6, 5 pages (Dec. 1996).
Henriksson, L. et al., A Urodynamic Evaluation of the Effects of Abdominal Urethrocystopexy and Vaginal Sung Urethroplasty in Women With Stress Incontinence, Am. J. Obstet. Gynecol. vol. 131, No. 1, pp. 77-82 (Mar. 1, 1978).
Hodgkinson, C. Paul et.al., Urinary Stress Incontinence in the Female, Department of Gynecology and Obstetrics, Henry Ford Hospital, vol. 10, No. 5, p. 493-499, (Nov. 1957).
Holschneider, C. H., et al., The Modified Pereyra Procedure in Recurrent Stress Urinary Incontinence: A 15-year Review, Obstetrics & Gynecology, vol. 83, No. 4, pp. 573-578 (Apr. 1994).
Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648-652 (Apr. 1998).
Ingelman-Sunberg, A. et al., Surgical Treatment of Female Urinary Stress Incontinence, Contr. Gynec. Obstet., vol. 10, pp. 51-69 (1983).
Jeffcoate, T.N.A. at al., The Results of the Aldridge Sling Operation for Stress Incontinence, Journal of Obstetrics and Gynaecology, pp. 36-39 (1956).
Karram, Mickey et al., Patch Procedure: Modified Transvaginal Fascia Lata Sling for Recurrent for Severe Stress Urinary Incontinence, vol. 75, pp. 461-463 (Mar. 1990).
Kersey. J., The Gauze Hammock Sling Operation in the Treatment of Stress Incontintence, British Journal of Obstetrics and Gynaecology, vol. 90, pp. 945-949 (Oct. 1983).
Klutke, Carl et al., The Anatomy of Stress Incontinence: Magentic Resonance Imaging of the Female Bladder Neck and Urethra, The Journal of Urology, vol. 143, pp. 563-566 (Mar. 1990).
Klutke, John James et al., Transvaginal Bladder Neck Suspension to Cooper's ligament: A Modified Pereyra Procedure, Obstetrics & Gynecology, vol. 88, No. 2, pp. 294-296 (Aug. 1996).
Klutke, John M.D. et al, The promise of tension-free vaginal tape for female SUI, Contemporary Urology. 7 pages (Oct. 2000).
Korda, A. et al., Experience With Silastic Slings for Female Urinary Incontience, Aust NZ J. Obstet Gynecol, vol. 29, pp. 150-154 (May 1989).
Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).
Kovac, S. Robert, et al, Pubic Bone Suburethral Stabilization Sling: A Long Term Cure for SUI?, Contemporary OB/GYN, 10 pages (Feb. 1998).
Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).
Kovac, Stephen Robert, M.D., Cirriculum Vitae, pp. 1-33 (Jun. 18, 1999).
Leach, Gary E., et al., Female Stress Urinary Incontinence Clinical Guidelines Panel Report on Surgical Management of Female Stress Urinary Incontinence. American Urological Association, vol. 158, pp. 875-880 (Sep. 1997).

Leach, Gary E., MD, Bone Fixation Technique for Transvaginal Needle Suspension, Urology vol. XXXI, No. 5, pp. 388-390 (May 1988).
Lichtenstein, Irving L. et al, The Tension Free Hernioplasty. The American Journal of Surgery, vol. 157 pp. 188-193 (Feb. 1989).
Loughlin, Kevin R. et al., Review of an 8-Year Experience With Modifications of Endoscopic Suspension of the Bladder Neck for Female Stress Incontinence, The Journal of Urology, vol. 143, pp. 44-45 (1990).
Marshall, Victor Fray et al. The Correction of Stress Incontinence by Simple Vesicourethral Suspension, Surgery, Gynecology and Obstetrics, vol. 88, pp. 509-518 (1949).
McGuire, Edward J. et al., Pubovaginal Sling Procedure for Stress Incontinence, The Journal of Urology, vol. 119, pp. 82-84 (Jan. 1978).
McGuire, Edward J. et al., Abdominal Procedures for Stress Incontinence, Urologic Clinics of North America, pp. 285-290, vol. 12, No. 2 (May 1985).
McGuire, Edward J. et al., Experience With Pubovaginal Slings for Urinary Incontinence at the University of Michigan, Journal of Urology, vol. 138, pp. 90-93(1987).
McGuire, Edwared J., M.D., The Sling Procedure for Urinary Stress Incontinence, Profiles in Urology, pp. 3-18.
McGuire, Edwared J. et al., Abdominal Fascial Slings, Slings, Raz Female Urology, p. 369-375 (1996).
McIndoe, G. A. et al., The Aldridge Sling Procedure in the Treatment of Urinary Stress Incontinence, Aust. N Z Journal of Obstet Gynecology, pp. 238-239 (Aug. 1987).
McKiel, Charles F. Jr., et al, Marshall-Marchetti Procedure Modification, vol. 96, pp. 737-739 (Nov. 1966).
Moir, J. Chesser et.al., The Gauze-Hammock Operation, The Journal of Obstetrics and Gynaecology of British Commonwealth, vol. 75 No. 1, pp. 1-9 (Jan. 1968).
Morgan, J. E., A Sling Operation, Using Marlex Polypropylene Mesh, for the Treatment of Recurrent Stress Incontinence, Am. J. Obst. & Gynecol, pp. 369-377 (Feb. 1970).
Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).
Narik, G. et.al., A Simplified Sling Operation Suitable for Routine Use, Gynecological and Obstetrical Clinic, University of Vienna, vol. 84, No. 3, p. 400-405, (Aug. 1, 1962).
Nichols, David H., The Mersilene Mesh Gauze-Hammock for Severe Urinary Stress Incontinence, Obstetrics and Gynecology, vol. 41, pp. 88-93 (Jan. 1973).
Norris, Jeffrey P. et al., Use of Synthetic Material in Sling Surgery: A Minimally Invasive Approach, Journal of Endourology, vol. 10. pp. 227-230 (Jun. 1996).
O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).
Ostergard, Donald R. et al., Urogynecology and Urodynamics Theory and Practice, pp. 569-579 (1996).
Parra, R. O., et al, Experience With a Simplified Technique for the Treatment of Female Stress Urinary Incontinence, British Journal of Urology, pp. 615-617 (1990).
Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45-50 (1999).
Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).
Pereyra, Armand J., M.D., F.A.C.S., A Simplified Surgical Procedure for Correction of Stress Incontinence in Women, West.J.Surg., Obst. & Gynec, p. 223-226, (Jul.-Aug. 1959).
Peter E. Papa Petros et al., Cure of Stress Incontinence by Repair of External Anal Sphincter, Acta Obstet Gynecol Scand, vol. 69, Sup 153, p. 75 (1990).

(56) References Cited

OTHER PUBLICATIONS

Peter Petros et al., Anchoring the Midurethra Restores Bladder-Neck Anatomy and Continence, The Lancet, vol. 354, pp. 997-998 (Sep. 18, 1999).
Petros, Peter E. Papa et al., An Anatomical Basis for Success and Failure of Female Incontinence Surgery, Scandinavian Journal of Neurourology and Urodynamics, Sup 153, pp. 55-60 (1993).
Petros, Peter E. Papa et al., An Analysis of Rapid Pad Testing and the History for the Diagnosis of Stress Incontinence, Acta Obstet Gynecol Scand, vol. 71, pp. 529-536 (1992).
Petros, Peter E. Papa et al., An Integral Therory of Female Urinary Incontinence, Acta Obstetricia et Gynecologica Scandinavica, vol. 69 Sup. 153, pp. 7-31 (1990).
Petros, Peter E. Papa et al., Bladder Instability in Women: A Premature Activation of the Micturition Reflex, Scandinavian Journal of Neurourology and Urodynamics, Sup 153, pp. 235-239 (1993).
Petros, Peter E. Papa et al., Cough Transmission Ratio: An Indicator of Suburethral Vaginal Wall Tension Rather Than Urethral Closure?, Acta Obstet Gynecol Scand, vol. 69, Sup 153, pp. 37-39 (1990).
Petros, Peter E. Papa et al., Cure of Urge Incontinence by the Combined Intravaginal Sling and Tuck Operation, Acta Obstet Gynecol Scand, vol. 69, Sup 153, pp. 61-62 (1990).
Petros, Peter E. Papa et al., Further Development of the Intravaginal Slingplasty Procedure—IVS III—(With Midline "Tuck"), Scandinavian Journal of Neurourology and Urodynamics, Sup 153, p. 69-71 (1993).
Petros, Peter E. Papa et al., Medium-Term Follow-Up of the Intravaginal Slingplasty Operation Indicates Minimal Deterioration of Urinary Continence With Time, (3 pages) (1999).
Petros, Peter E. Papa et al., Non Stress Non Urge Female Urinary Incontinence—Diagnosis and Cure: A Preliminary Report, Acta Obstet Gynecol Scand, vol. 69, Sup 153, pp. 69-70 (1990).
Petros, Peter E. Papa et al., Part I: Theoretical Morphological, Radiographical Correlations and Clinical Perspective, Scandinavian Journal of Neurourology and Urodynamics, Sup 153, pp. 5-28 (1993).
Petros. Peter E. Papa et al., Part II: The Biomechanics of Vaginal Tissue and Supporting Ligaments With Special Relevance to the Pathogenesis of Female Urinary Incontinence, Scandinavian Journal of Neurourology and Urodynamics. Sup 153, pp. 29-40 plus cover sheet (1993).
Petros, Peter E. Papa et al., Part III: Surgical Principles Deriving From the Theory, Scandinavian Journal of Neurourology and Urodynamics, Sup 153. pp. 41-52 (1993).
Petros, Peter E. Papa et at., Part IV: Surgical Appliations of the Theory—Development of the Intravaginal Sling Pklasty (IVS) Procedure, Scandinavian Journal of Neurourology and Urodynamics, Sup 153, pp. 53-54 (1993).
Petros, Peter E. Papa et al., Pinch Test for Diagnosis of Stress Urinary Incontinence, Acta Obstet Gynecol Scand, vol. 69, Sup 153, pp. 33-35 (1990).
Petros, Peter E. Papa at al., Pregnancy Effects on the Intravaginal Sling Operation, Acta Obstet Gynecol Scand, vol. 69, Sup 153, pp. 77-79 (1990).
Petros, Peter E. Papa et al., The Autogenic Ligament Procedure: A Technique for Planned Formation of an Artificial Neo-Ligament, Acta Obstet Gynecol Scand, vol. 69, Sup 153, pp. 43-51 (1990).
Petros, Peter E. Papa et al., The Combined Intravaginal Sling and Tuck Operation an Ambulatory Procedure for Cure of Stress and Urge Incontinence, Acta Obstet Gynecol Scand, vol. 69, Sup 153, pp. 53-59 (1990).
Petros, Peter E. Papa et al., The Development of the Intravaginal Slingplasty Procedure: IVS II—(With Bilateral "Tucks"), Scandinavian Journal of Neurourology and Urodynamics, Sup 153, pp. 61-67 (1993).
Petros, Peter E. Papa et al., The Free Graft Procedure for Cure of the Tethered Vagina Syndrome, Scandinavian Journal of Neurourology and Urodynamics, Sup 153, pp. 85-87(1993).

Petros, Peter E. Papa et al., The Further Development of the Intravaginal Slingplasty Procedure—IVS IV—(With "Double Breasted" Unattached Vaginal Flap Repair and "Free" Vaginal Tapes), Scandinavian Journal of Neurourology and Urodynamics, Sup 153, p. 73-75 (1993).
Petros, Peter E. Papa et al., The Further Development of the Intravaginal Slingplasty Procedure—IVS V—(With "Double Breasted" Unattached Vaginal Flap Repair and Permanent Sling)., Scandinavian Journal of Neurourology and Urodynamics, Sup 153, pp. 77-79 (1993).
Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81-84 (1993).
Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pp. 89-93 (1993).
Petros, Peter E. Papa et al., The Role of a Lax Posterior Vaginal Fornix in the Causation of Stress and Urgency Symptoms: A Preliminary Report, Acta Obstet Gynecol Scand, vol. 69, Sup 153, pp. 71-73 (1990).
Petros, Peter E. Papa et al., The Tethered Vagina Syndrome, Post Surgical Incontinence and I-Plasty Operation for Cure, Acta Obstet Gynecol Scand, vol. 69, Sup 153, pp. 63-67 (1990).
Petros, Peter E. Papa at al., The Tuck Procedure: A Simplified Vaginal Repair for Treatment of Female Urinary Incontinence, Acta Obstet Gynecol Scand, vol. 69, Sup 153, pp. 41-42 (1990).
Petros, Peter E. Papa et al., Urethral Pressure Increase on Effort Originates From Within the Urethra, and Continence From Musculovaginal Closure, Scandinavian Journal of Neurourology and Urodynamics, pp. 337-350 (1995).
Petros, Peter E. Papa, Development of Generic Models for Ambulatory Vaginal Surgery—Preliminary Report,International Urogynecology Journal, pp. 20-27 (1998).
Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270-278, (1997).
Rackley, Raymond R. et al., Tension-Free Vaginal Tape and Percutaneous Vaginal Tape Sling Procedures, Techniques in Urology, vol. 7, No. 2, pp. 90-100(2001).
Rackley, Raymond R. M.D., Synthetic Sungs: Five Steps for Successful Placement, Urology Times, p. 46,48,49 (Jun. 2000).
Raz, Shlomo, et al., The Raz Bladder Neck Suspension Results in 206 Patients, The Journal of Urology, pp. 845-846 (1992).
Raz, Shlomo, Female Urology, pp. 80-86, 369-398, 435-442 (1996).
Raz, Shlomo, MD. Modified Bladder Neck Suspension for Female Stress Incontinence, Urology, vol. XVII, No. 1, pp. 82-85 (Jan. 1981).
Richardson, David A. et al., Delayed Reaction to the Dacron Buttress Used in Urethropexy, The Journal of Reproductive Medicine. pp. 689-692, vol. 29, No. 9 (Sep. 1984).
Ridley, John H., Appraisal of the Goebell-Frangenheim-Stoeckel Sling Procedure, American Journal Obst & Gynec., vol. 95, No. 5, pp. 741-721 (Jul. 1. 1986).
Roberts, Henry, M.D., Cystourethrography in Women, Deptment of Obstetrics and Gynaecology, University of Liverpool, May 1952, vol. XXXV, No. 293, pp. 253-259.
Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).
Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).
Stamey, Thomas A., M.D., Endoscopic Suspension of the Vesical Neck for Urinary Incontinence in Females, Ann. Surgery, vol. 192 No. 4, pp. 465-471 (Oct. 1980).

(56) References Cited

OTHER PUBLICATIONS

Stanton, Stuart L., Suprapubic Approaches for Stress Incontinence in Women, Journal of American Geriatrics Society, vol. 38, No. 3, pp. 348-351 (Mar. 1990).

Stanton, Stuart, Springer-Veglag, Surgery of Female Incontinence, pp. 105-113 (1986).

Staskin, David R. et al., The Gore-Tex Sling Procedure for Female Sphincteric Incontinence: Indications, Technique, and Results, World Journal of Urology, vol. 15, pp. 295-299 (1997).

Studdiford, William E., Transplantation of Abdominal Fascia for the Relief of Urinary Stress Incontinence, American Journal of Obstetrics and Gynecology, pp. 764-775 (1944).

TVT Tension-free Vaginal Tape, Gynecare, Ethicon, Inc., 23 pages (1999).

Ulmsten, U. et al., A Multicenter Study of Tension-Free Vaginal Tape (TVT) for Surgical Treatment of Stress Urinary Incontinence, International Urogynecology Journal, vol. 9, pp. 210-213 (1998).

Ulmsten, U. et al., An Ambulatory Surgical Procedure Under Local Anesthesia for Treatment of Female Urinary Incontinence, International Urogynecology Journal. vol. 7, pp. 81-86 (May 1996).

Ulmsten, U., Female Urinary Incontinence—A Symptom, Not a Urodynamic Disease. Some Theoretical and Practical Aspects on the Diagnosis a Treatment of Female Urinary Incontinence, International Urogynecology Journal. vol. 6, pp. 2-3 (1995).

Ulmsten, U., Female Urinary Incontinence—A Symptom, Not a Urodynamic Disease. Some Theoretical and Practical Aspects on the Diagnosis a Treatment of Female Urinary Incontinence, International Urogynecology Journal, vol., 1995.

Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).

Ulmsten, Ulf et al., Different Biochemical Composition of Connective Tissue in Continent, Acta Obstet Gynecol Scand, pp. 455-457 (1987).

Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).

Ulmsten, Ulf et al., The Unstable Female Urethra, Am. J. Obstet. Gynecol., vol. 144 No. 1, pp. 93-97 (Sep. 1, 1982).

Vesica® Percutaneous Bladder Neck Stabilization Kit, A New Approach to Bladder Neck Suspenison, Microvasive® Boston Scientific Corporation, 4 pages (1995).

Vesica® Sling Kits, Simplifying Sling Procedures, Microvasive® Boston Scientific Corporation, 4 pages (1998).

Walters, Mark D., Percutaneous Suburethral Slings: State of the Art, Presented at the conference of the American Urogynecologic Society, Chicago, 29 pages (Oct. 2001).

Waxman, Steve et al., Advanced Urologic Surgery for Urinary Incontinence, The Female Patient, pp. 93-100. vol. 21 (Mar. 1996).

Webster, George D., Female Urinary Incontinence, Urologic Surgery, pp. 665-679, 1983.

Webster, George et al., Voiding Dysfunction Following Cystourethropexy: Its Evaluation and Management, The Journal of Urology, vol. 144, pp. 670-673 (Sep. 1990).

Winter, Chester C., Peripubic Urethropexy for Urinary Stress Incontinence in Women, Urology. vol. XX, No. 4, pp. 408-411 (Oct. 1982).

Woodside, Jeffrey R. et al., Suprapubic Endoscopic Vesical Neck Suspension for the Management of Urinary Incontinence in Myelodysplastic Girls, The Journal of Urology, vol. 135, pp. 97-99 (Jan. 1986).

Zacharin, Robert et at., Pulsion Enterocele: Long-Term Results of an Abdominoperineal Technique, Obstetrics & Gynecology, vol. 55 No. 2, pp. 141-148 (Feb. 1980).

Zacharin, Robert, The Suspensory Mechanism of the Female Urethra, Journal of Anatomy, vol. 97, Part 3, pp. 423-427 (1963).

Zimmem, Phillippe E. et al., Four-Corner Bladder Neck Suspension, Vaginal Surgery for the Urologist, vol. 2, No. 1, pp. 29-36 (Apr. 1994).

* cited by examiner

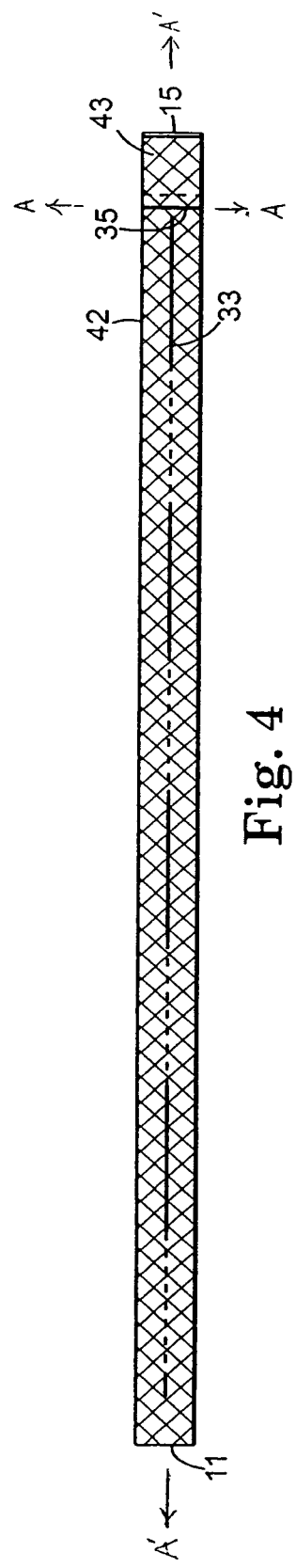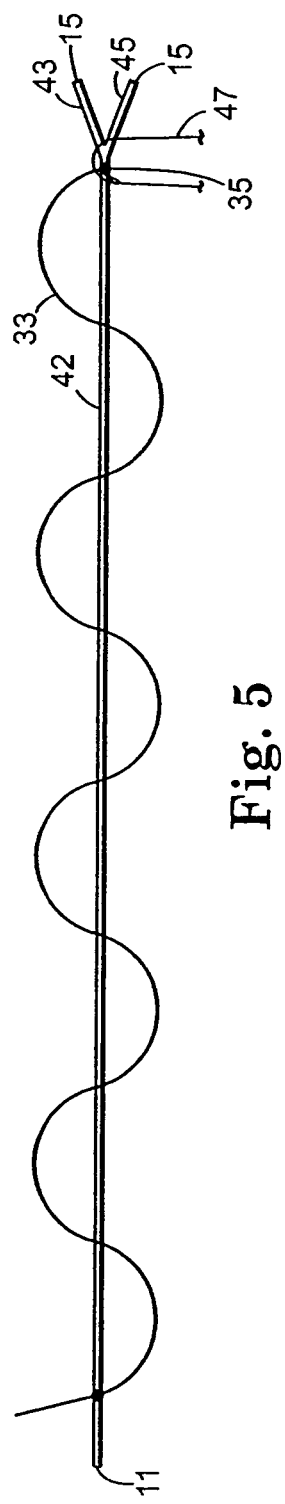
Fig. 4
Fig. 5

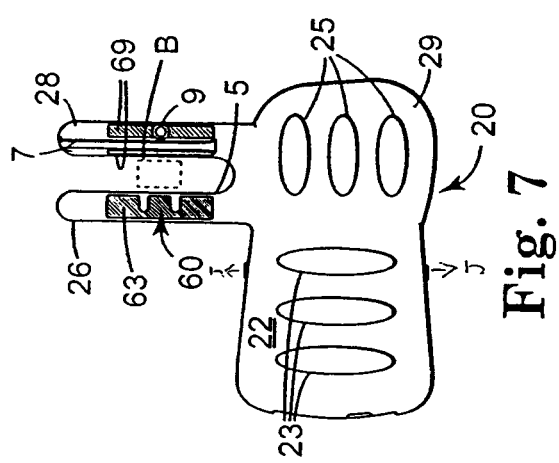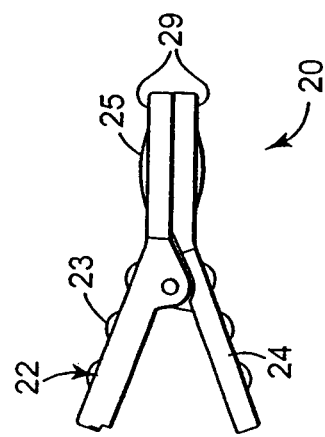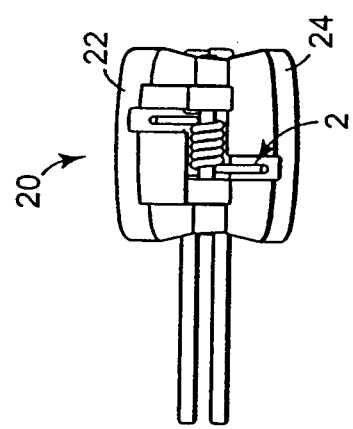

PELVIC FLOOR IMPLANT SYSTEM AND METHOD OF ASSEMBLY

CROSS REFERENCE TO RELATED APPLICATIONS

The present application is a continuation of U.S. patent application Ser. No. 10/335,119, filed Dec. 31, 2002, which is a continuation-in-part of U.S. patent application Ser. No. 10/106,086, filed Mar. 25, 2002, and U.S. patent application Ser. No. 10/306,179 filed Nov. 27, 2002, and U.S. patent application Ser. No. 10/280,945, filed Oct. 25, 2002 (which is a continuation of U.S. patent application Ser. No. 10/005,837 filed Nov. 9, 2001); and U.S. patent application Ser. No. 09/917,445 filed Jul. 27, 2001 (the "Parent Applications") and claims priority thereto and to U.S. Provisional Application Ser. No. 60/405,139, filed Aug. 22, 2002, which Parent Applications claim priority to U.S. Provisional Application Ser. No. 60/263,472, filed Jan. 23, 2001; and U.S. Provisional Application Ser. No. 60/269,829, filed Feb. 20, 2001, and U.S. Provisional Application Ser. No. 60/281,350, filed Apr. 4, 2001; and U.S. Provisional Application Ser. No. 60/295,068, filed Jun. 1, 2001, and U.S. Provisional Application No. 60/306,915, filed Jul. 20, 2001, and U.S. Provisional Patent Application No. 60/332,330 filed Nov. 20, 2001, and U.S. Provisional Application Ser. No. 60/362,806, filed Mar. 7, 2002; and U.S. Provisional Application Ser. No. 60/380,797, filed May 14, 2002; and U.S. Provisional Application Ser. No. 60/402,007, filed Aug. 8, 2002; and U.S. Provisional Application Ser. No. 60/414,865 filed Sep. 30, 2002, and U.S. Provisional Application Ser. No. 60/279,794, filed Mar. 29, 2001; and U.S. Provisional Application Ser. No. 60/302,929, filed Jul. 3, 2001; and U.S. Provisional Application Ser. No. 60/307,836, filed Jul. 25, 2001, and U.S. Provisional Application Ser. No. 60/322,309, filed Sep. 14, 2001. The entire contents of the provisional patent applications and Parent Applications are herein incorporated by reference.

BACKGROUND

Urinary incontinence is a significant health concern worldwide. Millions of people worldwide suffer from this problem. There are many different forms of incontinence. One of the most common is known as stress urinary incontinence (hereafter SUI).

A pubovaginal sling procedure is a surgical method involving the placement of a sling to stabilize or support the bladder neck or urethra. There are a variety of different sling procedures. Descriptions of different sling procedures are disclosed in U.S. Pat. Nos. 5,112,344; 5,611,515; 5,842,478; 5,860,425; 5,899,909; 6,039,686; 6,042,534 and 6,110,101.

Slings for treating incontinence may be constructed from synthetic materials such as polypropylene, polytetrafluoroethylene, polyester and silicone. Slings constructed from non-synthetic materials include allografts, homografts, heterografts, autologous tissues, cadaveric fascia and fascia lata. The strength and other properties of certain non-synthetic sling materials have been reported in the literature. See, Chaikin et al., *Weakened Cadaveric Fascial Sling: An Unexpected Cause of Failure*, Journal of Urology, Vol. 160, 2151 (December 1998); Choe et al., *Autologous, Cadaveric, and Synthetic Materials Used in Sling Surgery: Comparative Biomechanical Analysis*; Urology 58 (3), Pps. 482-86; 2001; and Lemer et al., *Tissue Strength Analysis of Autologous and Cadaveric Allografts of the Pubovaginal Sling*, Neurology and Urodynamics 18:497-503 (1999). While some non-synthetic sling materials are generally preferred by surgeons and patients, the quality of some non-synthetic materials (e.g. cadaveric sling material) varies greatly.

The supply of non-synthetic materials for slings varies greatly. Certain sizes of non-synthetic materials can be especially difficult to secure in a timely fashion. For example, autologous material may be difficult or impossible to harvest from some patients due to a variety of factors, including the health of the patient and the size of the tissue needed for a sling.

Some surgeons prefer synthetic materials, as they are readily available. The influence of various sling materials on tissue has been investigated. See Ulmsten et al., *Intravaginal Slingplasty (IVS): An Ambulatory Surgical Procedure For Treatment of Female Urinary Incontinence*, Scand. J. Urol. Nephrol 29: 75-82 (1995); Falconer et al., *Influence of Different Sling Materials on Connective Tissue Metabolism in Stress Urinary Incontinent Women*, Int. Urogynecol. J. (2001) (Suppl. 2): S19-S23; and Bent et al., *Tissue Reaction to Expanded Polytetrafluoroethylene Suburethral Sling for Urinary Incontinence: Clinical and Histological Study*, Am. J. Obstet. Gynecol., Vol 169, No. 5 Pps. 1198-1204 (1993).

Other relative advantages and disadvantages exist between non-synthetic and synthetic sling materials.

Some surgical procedures for incontinence utilize autologous tissue to provide a sling. See Aldridge, *Transplantation of Fascia for Relief of Urinary Stress Incontinence*, Am. J. of Obstetrics and Gynecology, v. 44, pages 398-411 (1948). There are significant recovery and morbidity issues associated with harvesting the sling material from the patient. See Sloane et al., *Stress Incontinence of Urine: A Retrospective Study of the Complications and Late Results of Simple Suprapubic Suburethral Fascial Slings*, J. of Urology, vol. 110, Pps. 533-536 (1973).

Some pubovaginal sling procedures extend a sling from the rectus fascia in the abdominal region, to a position below the urethra, and back again to the rectus fascia. Some slings are anchored in the abdominal fascia by virtue of suturing the sling material to the patient's abdominal tissue (e.g. rectus fascia). See Blaivas, *Commentary: Pubovaginal Sling Procedure*, Current Operative Urology, Edited by E. D. Whitehead, Philadelphia: J. B. Lippincott Co. Pp. 93-100 (1990) (biologic sling); and Moir, *The Gauze-Hammock Operation*, The Journal of Obstetrics and Gynaecology of the British Commonwealth, Vol. 75, No. 1, Pps. 1-9 (1968) (synthetic implant). Although serious complications associated with sling procedures are infrequent, they do occur. Complications include urethral obstruction, prolonged urinary retention, bladder perforations, damage to surrounding tissue, and sling erosion.

The Tension-free Vaginal Tape (TVT) procedure (available from Ethicon, of N.J.) utilizes a Prolene™ nonabsorbable, polypropylene mesh. The TVT mesh extends from the rectus fascia in the abdominal region, to a position below the urethra, and back again to the rectus fascia. No suture is recommended to tie the end of the mesh to the rectus fascia. Problems with the TVT procedure are documented in the literature and patents. See PCT publication nos. PCT WO 00/74613 and PCT WO 00/74594, U.S. Pat. Nos. 6,273,852; 6,406,423; and 6,478,727, and published U.S. Pat. Application Nos. 2002-0091373-A1, 2002-0107430-A1, 2002-0099258-A1 and US-2002-0099259-A1. See also, Walters, Mark D., *Percutaneous Suburethral Slings: State of the Art*, presented at the conference of the American Urogynecologic Society, Chicago (October 2001) and PCT International Publication No. WO 02/26108.

Additional sling procedures are disclosed in Published U.S. Pat. Appl. No. US 2001/0018549A1, and PCT Publication Nos. WO 02/39890 and WO 02/069781.

PCT Published Application No. WO 00/74633 discloses a tape for treating SUI. The tape is a combination of synthetic materials and a natural material centered between the synthetic materials. The natural material may be placed over or incorporated within a generally central portion of the synthetic material. The natural material may be connected to the synthetic material by sewing, a bio-compatible glue or cell culturing techniques.

Published U.S. Pat. Appl. No. 2002/0099260 discloses an implantable device or tape for use in correcting urinary incontinence. The tape includes sprayed polypropylene fibers that result in a strong implantable device. The tape also has a silicone-coated portion and tapered free ends.

U.S. Pat. No. 6,306,079 discloses a mesh pubovaginal sling comprising two pieces. One piece comprises a polypropylene mesh and a second mesh portion comprises an absorbable material such as poly-dioxanone. One piece may be inserted at the endopelvic fascia and the other in the suprapubic region. The two pieces are then connected via suture to support prolapsed organs so as to relieve urinary stress incontinence.

U.S. Pat. No. 6,355,065 discloses an implantable support that may be used in suburethral stabilization procedures for reducing stress incontinence. Ends of the support are folded to reinforce suture holes and to inhibit fraying or rupturing. Threading mechanisms may be provided to facilitate threading of sutures through suture holes. A removable, elongated clip may be placed on an intermediate portion of the implant to inhibit folding of the implant about its longitudinal axis. This document speculates that longitudinal folding of the implant could cause dead space in which bacteria could collect.

U.S. Pat. No. 6,042,534 discloses a stabilization sling for use in minimally invasive pelvic surgery. The sling may include reinforced suture receiving sites. Ends of the sling may be folded over to reinforce the sling.

PCT International Publication No. WO 02/28312 discloses a sub-urethral supporting assembly for treating female SUI. A junction part is disclosed for connecting two ends of a support tape.

Published U.S. Pat. Application No. 2002/0028980 discloses a Y-shaped implantable article for use in a sacral colpopexy procedure. Published U.S. Pat. Application No. 2002/0082619 discloses a reinforcing fastener guide for enhancing the functional longevity of an implant such as a sling.

SUMMARY OF THE INVENTION

The present invention comprises kit configurations, composite implants such as slings for treating pelvic floor disorders such as incontinence, surgical articles for assembling the implants and surgical methods.

In one aspect, the present invention comprises a surgical kit for use in assembling a composite implant for treating incontinence. The kit comprises a biocompatible synthetic material suitable for forming a first portion of the implant, and an implant assembly tool for association with the synthetic material for holding the synthetic material while a different biocompatible implant material is attached to an integration end of the synthetic material. Notably, the composite slings of the present invention comprise two different materials. The different materials may comprise synthetic and non-synthetic (e.g. porcine tissue) materials, absorbable and non-absorbable materials, a biomaterial and synthetic material, a tissue engineered biomaterial and a non-tissue engineered biomaterial, combinations thereof, etc. They need not have at least one synthetic component.

In a preferred embodiment, the integration end of the synthetic material comprises a Y-shaped structure with a pair of leg portions and a seam. The implant assembly tool comprises first and second implant association jaws. Each jaw is preferably associated with a leg portion. The jaws are movable between an open position with the leg portions spaced apart to receive a different implant material therebetween, and a closed position with the leg portions spaced closer together than in the open position.

In another aspect, the invention is not limited to the inclusion of an implant assembly tool. In this embodiment, the invention comprises an assembly of components for use in constructing a composite sling for treating a patient's incontinence. The assembly comprises a first segment comprising a synthetic material having a distal end and an attachment end; a second segment comprising a synthetic material having a distal end and an attachment end; and an integrator for associating a biomaterial with the attachment ends of the first and second segments so that the biomaterial may be placed underneath the patient's urethra. In this aspect, the first and second segments are specially sized and shaped. For example, they may be sized and shaped to extend from a position substantially adjacent the patient's urethra to a position substantially adjacent the patient's rectus fascia so that the first and second segments and the biomaterial can provide a U-shaped sling extending from the patient's rectus fascia in the abdominal region, to a position below the patient's urethra, and back to the rectus fascia on an opposite side of the patient's urethra. Alternatively, they may be sized and shaped extend from a position substantially adjacent the patient's urethra to a position substantially adjacent the patient's obturator foramen so that the first and second segments and the biomaterial can provide a sling extending from a position substantially adjacent the patient's obturator foramen in the pelvic region, to a position below the patient's urethra, and to the patient's obturator foramen on an opposite side of the patient's urethra.

The present invention contemplates a wide variety of structures for serving as an integrator. In one embodiment, the integrator comprises Y-shaped portions at the attachment ends of the first and second segments. In this embodiment, the surgeon may join the biomaterial to the first and second segments by suturing them together. In another embodiment, the integrator comprises strengtheners. The strengtheners may comprise silicone integrated into the first and second segments. In another embodiment, the strengtheners may comprise suture anchors for the biomaterial. In another embodiment, the integrator may comprise a mechanical fastener such as a staple.

In a preferred embodiment, the first and second segments include a tensioning filament for adjusting placement of the sling within the patient. The tensioning filament is preferably attached to the synthetic material at a location substantially adjacent, yet spaced from legs of the Y-shaped portions. Also preferably, each of the first and second segments further include a removable loosening loop operatively associated with a tensioning filament. The removable loosening loop is adapted to be cut and removed once the implant is properly tensioned. The assembly may optionally include a convenient tab associated with the loosening loop. The loosening loop preferably includes a pair of knots so that when the loosening loop is cut, it may be removed from the synthetic segment (the sling) without a knot passing through the segment. Preferably, the loosening loop is looped around a seam of the Y-shaped portion to resist damage to a biomaterial of the sling and the attachment between the biomaterial and the synthetic material during adjustment of the placement of the sling within the patient.

In another aspect, the present invention comprises a novel implant assembly tool, particularly suitable for assembling a composite implant from a first biocompatible material and second biocompatible material that is different from the first material. The implant is preferably a sling for treating incontinence. The assembly tool comprises holders for retaining the first and second biocompatible materials in a substantially flat condition while the first and second biocompatible materials are attached, and a passageway for passage of a joiner for attaching the first material to the second material. The joiner may comprise a needle/suture combination chosen by the surgeon or it may comprise another joining element such as a staple, grommet, screw, mechanical fastener, biocompatible adhesive, pledget, or anchor.

The holders preferably comprise a pair of jaws. The first biocompatible material preferably comprises a Y-shaped structure described above. In this embodiment, each jaw is associated with a leg portion of the Y-shaped structure. The jaws are movable between an open position with the leg portions spaced apart to receive the second biocompatible material therebetween, and a closed position with the leg portions spaced closer together than in the open position. A seam of the Y-shaped portion preferably has an axis (e.g. one that is perpendicular to the longitudinal axis of the sling), and the jaws are mounted to pivot about an axis that is substantially parallel or colinear with the axis of the seam so that ends of the leg portions remain substantially parallel during movement between the open and closed positions.

The passageway of the assembly tool preferably comprises an open ended channel formed by tines. The channel is sized and shaped to afford passage of a suture and needle combination. Alternatively, the passageway may comprise a hole or other void.

In a preferred embodiment, the implant assembly tool is associated with the synthetic material by a suture that connects a tine to a leg portion. Alternatively, the implant assembly tool may be associated with the synthetic material by interaction between the structured surface and the synthetic material. For example, the structured surface may comprise hooks for a hook and loop type association between the implant assembly tool and the synthetic material.

In a preferred embodiment, a tine of each jaw includes a cutting slot adapted to receive a blade to guide the blade as it cuts the suture that associates the tine with a leg portion to separate the implant assembly tool from the synthetic material once the synthetic material is attached to the different implant material. Preferably, the suture that associates the tine with a leg portion includes a pair of knots so that when the suture is cut to release implant assembly tool from the leg portion, the suture remains with the implant assembly tool. Also in the preferred embodiment, the jaws include indicia for indicating preferred location of suture passage for attaching the synthetic material to the different implant material.

The jaws of the implant assembly tool preferably include manually engageable portions for grasping the sling assembly tool while the suture and needle combination is passed through the channel. This can contribute to the aseptic nature of the composite sling assembly. The tool also preferably includes biasing means (e.g. a coil spring) for biasing the jaws toward the closed position, and opening flanges for pressing on to move the jaws from the closed toward the open position against the bias of the spring.

In another aspect the present invention comprises novel surgical methods. In one embodiment, the surgical method comprises the steps of (1) providing a synthetic material suitable for use in forming a first portion of an implant, the first portion having a distal end and an attachment end, and a implant assembly tool for association with the synthetic material, (2) holding the synthetic material with the implant assembly tool, and (3) attaching a different implant material to the attachment end of the synthetic material.

In another embodiment, the invention comprises the steps of (1) providing a first segment comprising a synthetic material having a distal end and an attachment end; a second segment comprising a synthetic material having a distal end and an attachment end; (2) integrating a biomaterial with the attachment ends of the first and second segments so that the biomaterial may be placed underneath the patient's urethra, and (3) then implanting the first and second segments and the integrated biomaterial so that they provide a U-shaped sling extending from the patient's rectus fascia in the abdominal region, to a position below the patient's urethra, and back to the rectus fascia on an opposite side of the patient's urethra. Alternatively, step 3 may comprise a transobturator type surgical procedure comprising the step of: then implanting the first and second segments and the integrated biomaterial so that they provide a sling extending from a position substantially adjacent the patient's obturator foramen in the pelvic region, to a position below the patient's urethra, and to the patient's obturator foramen on an opposite side of the patient's urethra. In yet another alternative, step 3 can involve implanting the sling in the retropubic space without abdominal incisions (e.g. with the use of a bone anchor or alternatively, with a hemi-sling).

BRIEF DESCRIPTION OF THE DRAWINGS

Other features and advantages of the present invention will be seen as the following description of particular embodiments progresses in conjunction with the drawings, in which:

FIG. 4 is a top view of a segment of implantable material according to another aspect of the present invention;

FIG. 5 is a side view of FIG. 4;

FIG. 6 is a side view of an implant assembly tool according to another aspect of the present invention;

FIG. 7 is a top view of the implant assembly tool of FIG. 6;

FIG. 8 is an end view of the implant assembly tool of FIG. 6;

DETAILED DESCRIPTION

Figure 1:
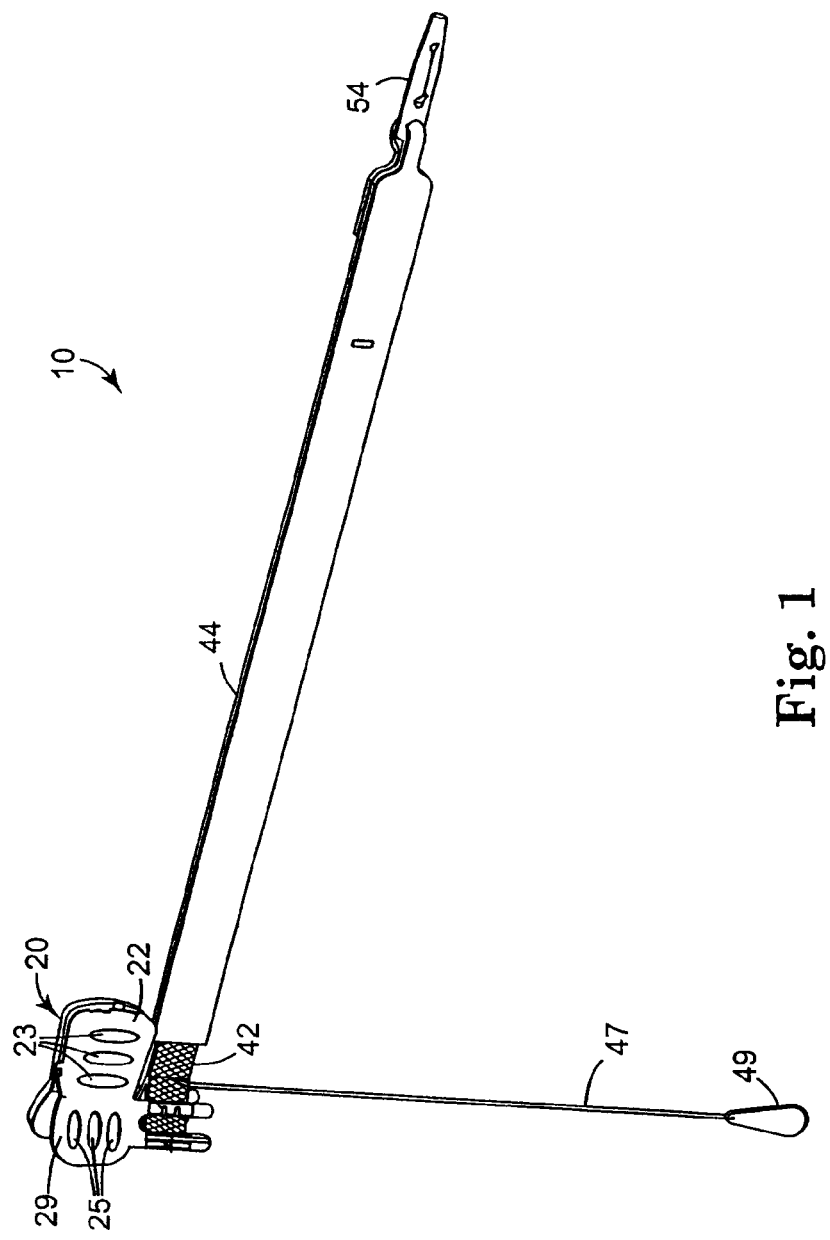
FIG. 1 is a perspective view of one embodiment of the present invention.

The following description is meant to be illustrative only and not limiting. Other embodiments of this invention will be apparent to those of ordinary skill in the art in view of this description.

The present invention is directed to surgical instruments, assemblies and implantable articles for treating pelvic floor disorders such as incontinence or stress urinary incontinence (SUI) in both men and women. The present invention is also directed to improved surgical procedures that utilize the surgical articles.

FIGS. 1 through 14 show components of an assembly 100 for constructing a composite implant (e.g. a sling) for treating incontinence, particularly SUI. The composite implant comprises a first material and a second material that is different from the first material. In a preferred embodiment, the first material comprises a synthetic material (e.g. 42) and the second material comprises a biomaterial (e.g. 50 in FIG. 22) or non-synthetic material. In another embodiment, one material comprises an absorbable material and the other material comprises a non-absorbable or permanent material. In another embodiment, the one portion may be resorbable or absorbable, another portion may be non-absorbable and another portion may be constructed of a different material. A naturally occurring biomaterial may be used or a tissue engineered material may be used. As used in this application, when it is said that one implant material is different than another implant material, it is meant that the materials substantially differ in a feature that can potentially affect a surgical procedure for treating a urological disorder, including the results. Features that can be different according to the present invention include, but are not limited to the ability of the sling to avoid infections or tissue (urethral) erosion (actual or perceived), the shelf life of the material, the type of material, the shape of the material, the presence of a sling tensioning member (e.g. as disclosed in U.S. patent application Ser. No. 09/917,562, filed Jul. 27, 2001), the present of a sling adjustment feature as described in U.S. patent application Ser. No. 10/004,185 filed Oct. 30, 2001, sling material treatment, the porosity of the sling material, the shape of the sling material, the sling length, the strength of the material, the elastic property of the material, the potential for tissue ingrowth, the biocompatibility of the material, and the presence or absence of a sheath.

Suitable non-synthetic materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium and fascia lata. Suitable synthetic materials for a sling include polymerics, metals (e.g. silver filigree, tantalum gauze mesh, and stainless steel mesh) and plastics and any combination of such materials.

Commercial examples of non-absorbable materials include Marlex™ (polypropylene) available from Bard of Covington, R.I., Prolene™ (polypropylene) and Mersilene (polyethylene terphthalate) Hernia Mesh available from Ethicon, of New Jersey, Gore-Tex™ (expanded polytetrafluoroethylene) available from W. L. Gore and associates, Phoenix, Ariz., and the polypropylene sling available in the SPARC™ sling system, available from American Medical Systems, Inc. of Minnetonka, Minn. Commercial examples of absorbable materials include Dexon™ (polyglycolic acid) available from Davis and Geck of Danbury, Conn., and Vicryl™ available from Ethicon. Other examples of suitable materials include those disclosed in U.S. patent application Ser. No. 09/939,098 filed Aug. 24, 2001 and published U.S. Pat. Application No. 2002/0072694. More specific examples of synthetic sling materials include, but are not limited to polypropylene, cellulose, polyvinyl, silicone, polytetrafluoroethylene, polygalactin, Silastic, carbon-fiber, polyethylene, nylon, polyester (e.g. Dacron) PLLA and PGA.

The synthetic portions may be knitted, woven, sprayed or punched from a blank. Some slings may be sufficiently robust to be inserted without a protective sleeve. In other embodiments, some synthetic slings may have an associated sheath or sleeve 44 (described in greater detail below).

In one embodiment a synthetic portion may comprise a mesh material. The mesh material comprises one or more woven, knitted or inter-linked filaments or fibers that form multiple fiber junctions throughout the mesh. The fiber junctions may be formed via weaving, knitting, braiding, bonding, ultrasonic welding or other junction forming techniques, including combinations thereof. In addition, the size of the resultant openings or pores of the mesh may be sufficient to allow tissue in-growth and fixation within surrounding tissue. As an example, not intended to be limiting, the holes may comprise polygonal shaped holes with diagonals of 0.132 inches and 0.076 inches.

The quantity and type of fiber junctions, fiber weave, pattern, and material type influence various sling properties or characteristics. As another example, not intended to be limiting, the mesh may be woven polypropylene monofilament, knitted with a warp tricot. The stitch count may be 27.5 courses/inch (+ or −2 courses) and 13 wales/inch (+ or −2 wales). The thickness of this example is 0.024 inches. This embodiment of sling is preferably associated with a sleeve 44. Non-mesh sling configurations are also included within the scope of the invention.

The mesh 42 is preferably elastic, as opposed to the substantially inelastic mesh available in Europe as Uratape® from Porges, and the tape described in Published U.S. Pat. Appl. No. 2002/0099260. A test for defining whether a synthetic material is elastic is disclosed in U.S. patent application Ser. No. 10/306,179 filed Nov. 27, 2002.

Figure 2:
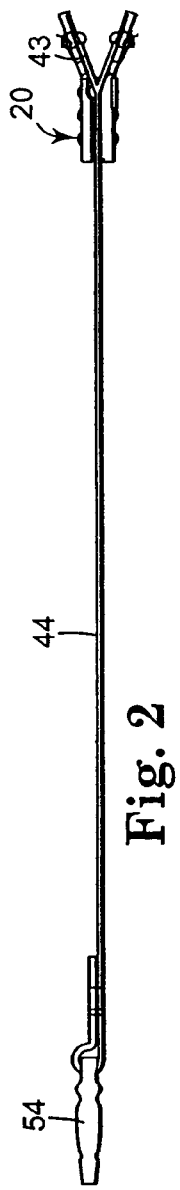
FIG. 2 is a reversed, bottom view of the embodiment of FIG. 1, showing an implant assembly tool in an open position.
Figure 3:
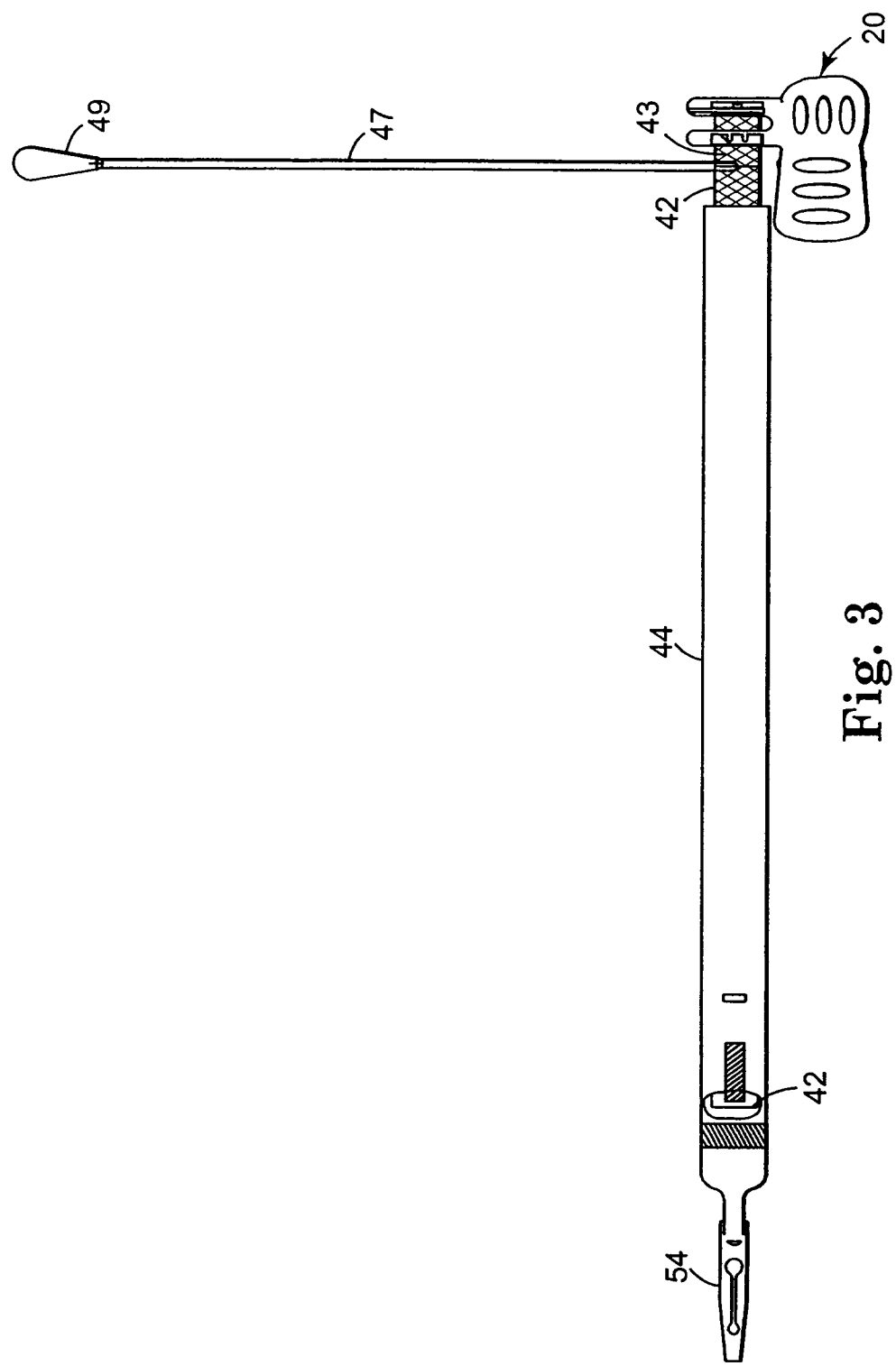
FIG. 3 is a bottom view of the embodiment of FIG. 2.

Referring to FIGS. 1 through 3, a sheath 44 is preferred when the sling 42 is elastic. After the sling is implanted, the sheath 44 is removed and discarded. Preferably, the sheath 44 is constructed of a material that affords visual examination of the implantable sling material 42 and that affords convenient passage through tissue of the patient.

In a preferred embodiment, the sheath 44 is made of polyethylene. Other materials including, without limitation, polypropylene, nylon, polyester or Teflon may also be used to construct the sheath 44. The sheath 44 should also conveniently separate from the sling material 42 after the sling 42 is implanted without materially changing the position of the sling 42.

As shown in FIGS. 1-3, a portion of the sling material 42 (e.g. including leg portions 43 and 45, described in greater detail below) projects from an end of the sheath 44. The length of this projection may comprise, for example, about an inch. Alternatively, the sheath 44 may comprise an extendable member that can be movable from i) a retracted position with a portion of the sling material projecting from an end of the sheath 44 to afford joining of the leg portions 43 and 44 to a biomaterial 50 (FIG. 22), to ii) an extended position with additional or all of the material of component 42 covered thereby. It is believed that extending the sheath over additional parts of the material of component 42 (e.g. seam 35) may afford a smoother transition at this position. An extendable sheath may be accomplished in a variety of fashions including Z-folding the sheath, constructing the sheath of a stretchable or expandable material, and the like.

The mid-portion of the assembled sling (the portion designed to reside underneath the urethra, preferably the mid urethra) is preferably substantially free of any silicone coatings. Alternative placements for the mid-portion are also contemplated herein, such as at the bladder neck or elsewhere. A variety of factors can influence the surgeon's decision, such as the presence or absence of scarring, the condition of the urethral tissue and other factors.

In another embodiment the sling material components may have one or more substances associated therewith through a process such as coating or they may be incorporated into the raw material of the sling. Examples of appropriate substances include, without limitation, drugs, hormones, antibiotics, antimicrobial substances, dyes, silicone elastomers, polyurethanes, radiopaque filaments or substances, anti-bacterial substances, chemicals or agents, including any combinations thereof. The substances may be used to enhance treatment effects, reduce potential sling rejection by the body, reduce the chances of tissue erosion, enhance visualization, indicate proper sling orientation, resist infection or other effects.

While the assembled slings are preferably substantially polygonal for treating SUI in females, other shapes are also contemplated. Depending on the treatment addressed (e.g. to provide hammock support for the bladder or bladder neck, or to address a rectocele, enterocele or prolapse) the slings may be any of a wide variety of shapes. Components 42 are preferably rectangular.

Suitable synthetic, non-synthetic, absorbable and non-absorbable biocompatible implant materials are disclosed in the conference proceedings of Julian, T M, *Vaginal Reconstruction Using Graft Materials*, 12$^{th}$ International Pelvic Reconstructive and Vaginal Surgery Conference, St. Louis, Mo., Sep. 25-28, 2002. A non-synthetic material may be constructed according to the teachings of U.S. Provisional Patent Appl. No. 60/405,139, filed Aug. 22, 2002. Other suitable materials for forming portions of the composite sling are described in published U.S. Pat. No. 2002-0138025-A1, published Sep. 26, 2002.

Figure 14:
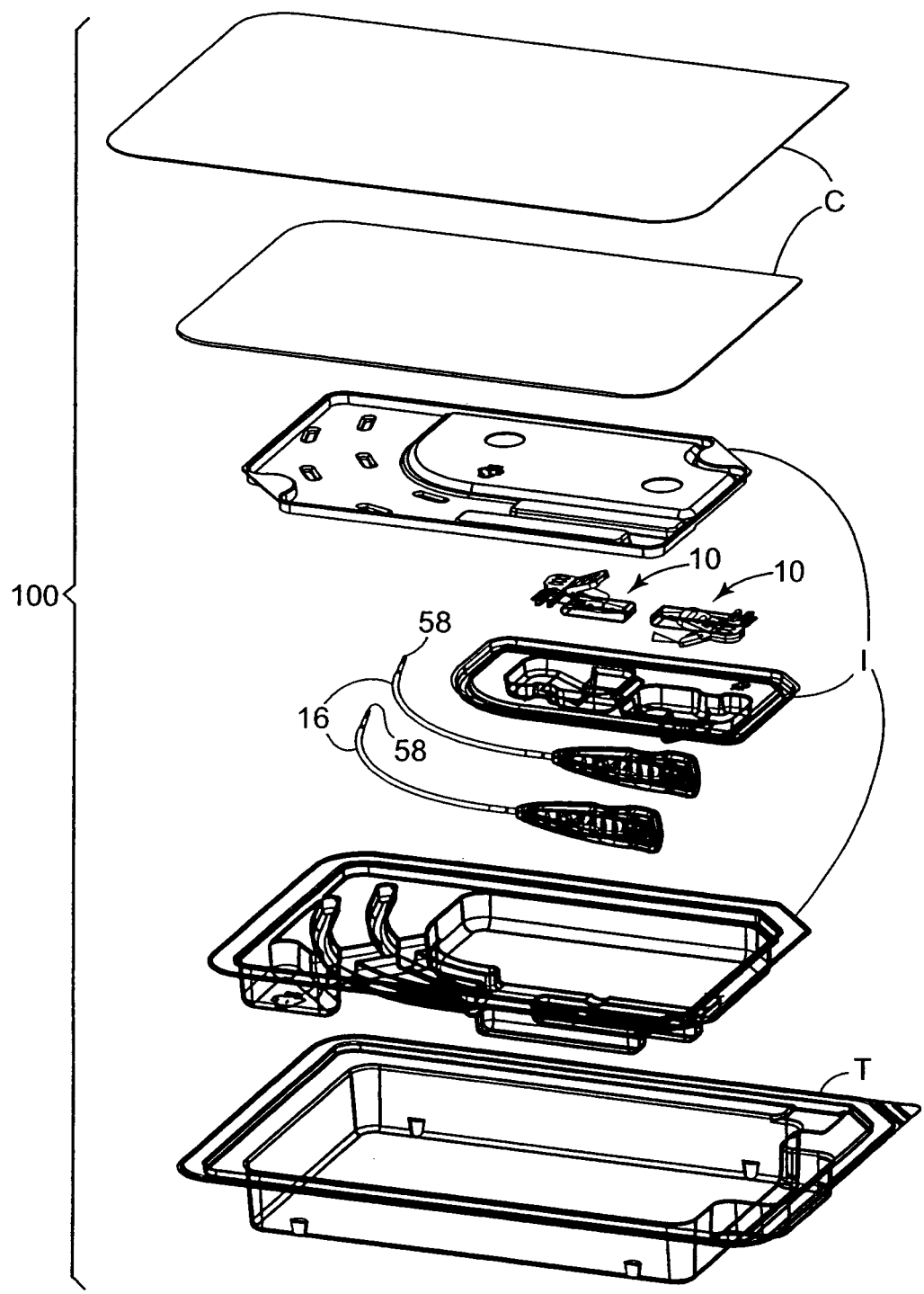
FIG. 14 is an exploded perspective view of a sterile kit according to an aspect of the present invention.

FIGS. 4 and 5 show a first material or segment 42 (preferably a synthetic mesh) suitable for forming a first portion of the implant. Assembly 100 (FIG. 14) includes sub assembly 10. Subassembly 10 includes a first segment comprising first material 42 (e.g. a synthetic material) with a distal end 11 and an attachment or integration end 15. The subassembly 10 also optionally includes sheath 44 and implant assembly tool 20. The first material 42 may be provided as part of a subassembly 10 which is described in greater detail below. As shown in FIG. 14, the assembly 100 preferably includes a second subassembly 10.

The segment 42 optionally has a tensioning filament or suture 33. Tensioning filaments are generally disclosed in U.S. Published Pat. Application No US-2002-0107430-A1. The particular tensioning suture 33 may be constructed from a permanent or absorbable material and is described in greater detail below.

The present invention also includes an integrator for associating a second type of material (e.g. a biomaterial) with the attachment ends 15 of first and second segments of material 42 so that the biomaterial may be placed underneath the patient's urethra.

In FIGS. 4 and 5, the integrator includes Y-shaped portion having leg portions 43 and 45 at the attachment end of segment 42. The leg portions 43 and 45 may be constructed in any suitable manner, such as creating a seam 35. The seam 35 may be created in any suitable fashion such as by suturing a piece of biocompatible material suitable for forming a leg 43 or 45 to the rest of the component 42, welding such a piece or adhering such a piece. The length of the legs 43 and 45 is preferably sufficient to afford convenient attachment to biomaterial (e.g. 50 FIG. 22). For example, the length may be between 0.25 and 1 inch, preferably about 0.5 inches. The width and thickness of the leg portions 43 and 45 is preferably similar to those of the rest of the component 42.

In the embodiment shown in FIGS. 4 and 5, the surgeon may join the biomaterial (e.g. 50 in FIG. 22) to the segment 42 by suturing them together at the Y-shaped portion. Alternatively, the integrator may comprises strengtheners such as silicone integrated into segment 42 and/or suture anchors or pledgets for the biomaterial. In another embodiment, a segment of the sling need not include a Y-shaped portion. Instead, ends of dissimilar sling materials may be brought into an abutting relationship and a mechanical fastener (e.g. a staple or the article disclosed in Published U.S. Pat. Application No. 2002/0082619) may be used to join the dissimilar pieces together. In yet another embodiment, one of the legs 43 or 45 may be of a material that is different than the rest of the component 42 and the biomaterial 50 to perform as a bridge between material 42 and material 50.

In one embodiment, the segments 42 are sized and shaped to extend from a position substantially adjacent the patient's urethra to a position substantially adjacent the patient's rectus fascia so that the first and second segments and the biomaterial can provide a U-shaped sling extending from the patient's rectus fascia in the abdominal region, to a position below the patient's urethra, and back to the rectus fascia on an opposite side of the patient's urethra.

In this embodiment, the sheath length of the assembly is approximately within the range of 24 cm to 30 cm, sheath width is approximately within the range of 1.0 cm to 2 cm, and sheath material thickness is approximately within the range of 0.127 mm to 0.203 mm, respectively. The associated sling mesh 42 has a length, width and thickness approximately within the range of 22 cm to 24 cm; 1.0 cm to 2 cm; and 0.508 mm to 0.711 mm, respectively. When a sheath is utilized, it is preferably connected to the mesh (e.g. by an ultrasonic weld or other suitable attachment method) adjacent an end of the mesh.

Alternatively, the overall dimensions of the assembly including sheath 44 and sling 42 may be selected for a transobturator type surgical procedure. The sheath and sling should be sufficient, when combined with a biomaterial for the mid portion, to extend from a superficial incision near the obturator fascia, to an undersurface of the urethra and then to another incision adjacent obturator fascia that is opposite the first incision. Alternatively, the skin incisions need not be made and the ends of the sling can rest underneath the skin. The size of the sling can take into account the imprecision associated with the range of human anatomy sizes. In one embodiment, the sheath length of the assembly is approximately within the range of 18 cm to 24 cm, sheath width is approximately within the range of 1.0 cm to 2 cm, and sheath material thickness is approximately within the range of 0.127 mm to 0.203 mm, respectively. The associated sling mesh has a length, width and thickness approximately within the range of 15 cm to 17 cm; 1.0 cm to 2 cm; and 0.508 mm to 0.711 mm, respectively.

In yet another embodiment, the assembled sling and/or components thereof may be designed for placement through the retropubic space of the patient without abdominal incisions. Such procedures are disclosed in U.S. Pat. No. 6,382,214, and published U.S. Pat. Application Nos. 2002/0161382 A1 and 2002/0128670 A1.

Referring to FIGS. 4 and 5, the segment 42 preferably includes a tensioning filament 33 for adjusting placement of the sling within the patient. The undulations of the tensioning filament 33 are exaggerated to show that it alternates between a first and a second major surface of the segment 42. However, filament 33 is preferably taught. The tensioning filaments 33 are preferably fixed at each end (e.g. 33') to the sling material (e.g. a polypropylene mesh) by welding (e.g. ultrasonic), knotting, anchoring, adhering (e.g. with and adhesive) or the like. They may comprise absorbable or non-absorbable sutures.

Figure 22:
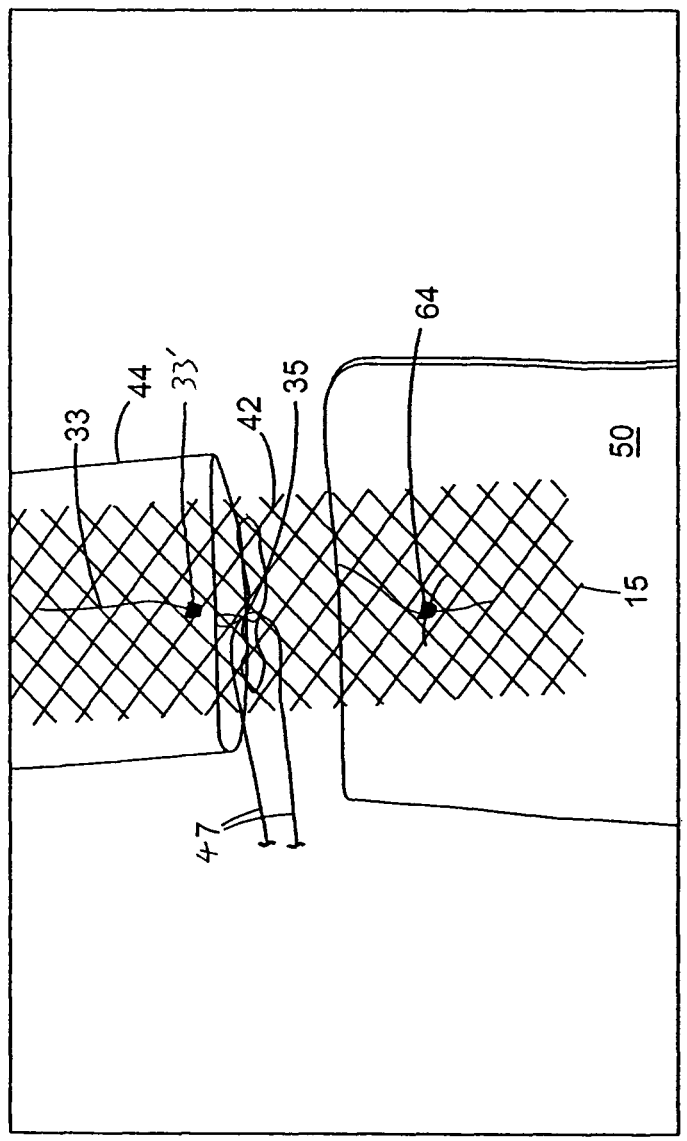
FIG. 22 is a schematic view showing a biomaterial sutured to a synthetic material after the implant assembly tool has been removed.

Referring to FIG. 22, the tensioning filament 33 is preferably attached to the synthetic material 42 at a location 33' substantially adjacent, yet spaced from legs 43 and 45 of the Y-shaped portions.

Referring to FIGS. 1, 3 and 5, the segments 42 optionally include a removable loosening loop 47 operatively associated with tensioning filament 33. The removable loosening loop 47 is adapted to be cut (e.g. with cutting instrument 57, see FIG. 23) and removed once the implant is properly tensioned.

The assembly may optionally include a convenient tab 49 associated with the loosening loop. The tab 49 may be constructed from a biocompatible material such as silicone. The tab 49 may be sized and shaped to receive a hemostat clamped thereto for the convenience of the surgeon.

Figure 13:
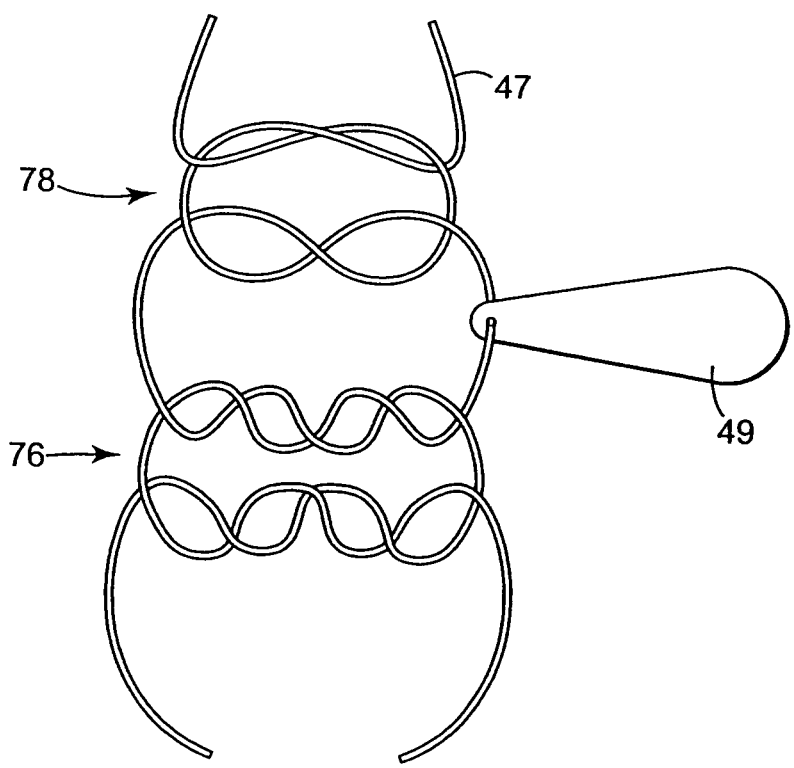
FIG. 13 is a plan view of a tab and portions of a loosening loop, showing knots being tied in the loosening loop on both sides of the tab.

Referring to FIG. 13, the loosening loop 47 preferably includes a pair of knots 76 and 78. The knots 76 and 78 are provided so that when the loosening loop 47 is cut (e.g. see FIG. 23), the loosening loop 47 may be removed from the synthetic segment 42 without a knot 76 or 78 and/or tab 49 passing through the segment 42. Preferably, the loosening loop 47 is looped around seam 35 of the Y-shaped portion to resist damage to biomaterial 50 and/or the attachment between the biomaterial 50 and the synthetic material 42 during adjustment of the placement of the sling within the patient, and or the attachment 33' of tensioning filament 33. As an example not intended to be limiting, knot 76 may comprise single throw overhand knots and knot 78 may comprise double throw overhand knots.

The subassemblies 10 may optionally includes sheath 44, a dilator 54 and an implant assembly tool 20 depending upon a variety of factors such as the specific needle used to insert the sling, the specific sling material(s), the presence or absence of concomitant procedures, the specific sling procedure contemplated, the configuration of the sling components (e.g. whether they include a Y-shaped end) and the specific integrator used. FIGS. 1 through 3 show a novel implant assembly tool 20 for association with the synthetic material 42 for holding the synthetic material 42 while a different implant material is attached to the integration end 15.

Assembly 100 may include a dilator 54 (FIG. 2) for use in a surgical sling procedure. The dilator is optional but present in some preferred embodiments. The dilator 54 comprises surfaces for associating the dilator with a needle (e.g. end 58 of needle 16).

The kit shown in FIG. 14 includes two dilators 54. The dilators 54 atraumatically create and/or expand the passageway through the tissues for sling assembly delivery. The tip or leading end of the dilator 54 is preferably blunt, as, in preferred embodiments, the leading tip of the dilator 54 will pass through tissue that has already been pierced by a needle 16. The dilator 54 may be made from a variety of biocompatible and sterilizable materials including, without limitation, acetal, polycarbonate, polypropylene, Delrin®, Acrylonitrile-Butadiene-Styrene (ABS), polyethylene, nylon and any combination of biocompatible materials.

The dilator 54 preferably includes means for associating with a surgical needle 16. In a preferred embodiment, the association means affords a permanent affixation between the dilator 54 and the needle 60. By "permanent affixation", it is meant that it would be very difficult to manually separate the dilator from the needle after they have become permanently affixed. After implantation of the sling, to separate the sling 42 from the dilator 54/needle 61, the surgeon cuts an end of the sling as described more fully below. The association means preferably affords quick and convenient attachment of the dilator 54 to the needle 16 to avoid wasting time in the midst of a surgical procedure. The attachment should also be secure to avoid separation of the needle 16 and dilator 54 while the combination is passed through tissue.

Details concerning various dilators are described in published U.S. Pat. Application Nos. 2002-0147382-A1, US-2002-0107430-A1 and US-2002-0151762-A1, and U.S. patent application Ser. No. 10/306,179 filed Nov. 27, 2002.

The assembly tool 20 comprises holders for retaining the first and second biocompatible materials in a substantially flat condition while the first 42 and second 50 biocompatible materials are attached, and a passageway 5 (FIG. 12) for passage of a joiner for attaching the first material 42 to the second material 59. The joiner may comprise a needle/suture combination 99 chosen by the surgeon or it may comprise another joining element such as a staple, grommet, screw, mechanical fastener, biocompatible adhesive, pledget, or anchor.

Figure 12:
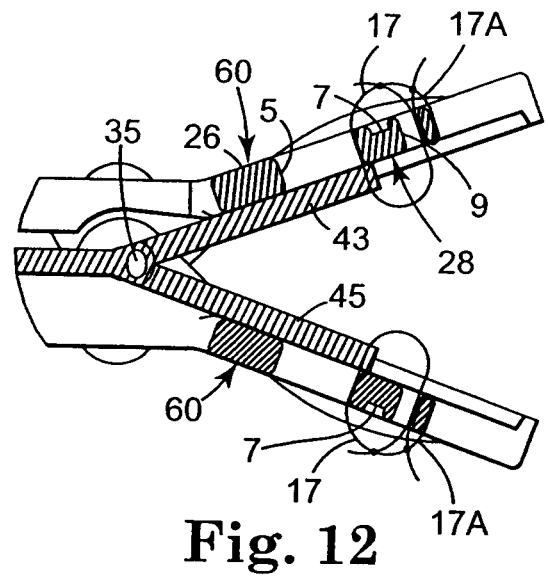
FIG. 12 is a side view of a portion of an implantable material within a portion of an implant assembly tool showing jaws of the implant assembly tool in an open position.

The holders preferably comprise a pair of jaws 60. The first biocompatible material 42 preferably comprises a Y-shaped structure described above. In this embodiment, each jaw 60 is associated with a leg portion 43 or 45 of the Y-shaped structure (FIG. 12). The jaws 60 are movable between an open position (FIG. 12) with the leg portions spaced apart to receive the second biocompatible material therebetween, and a closed position (e.g. FIGS. 17 and 18) with the leg portions 43 and 45 spaced closer together than in the open position.

Seam 35 has axis A (FIG. 4) that is perpendicular to the longitudinal axis A' of the sling. The jaws 60 are mounted to pivot about an axis J (FIG. 7) that is substantially parallel or colinear with the axis A of the seam 35 so that ends 15 of the leg portions 43 and 45 remain substantially parallel during movement between the open and closed positions. This contributes to a desired non-wrinkled joining of components 42 and 50.

The passageway 5 of the assembly tool 20 preferably comprises an open ended channel formed by tines 26 and 28. The channel is sized and shaped to afford passage of a suture and needle combination 99. The channel is preferably sufficiently large to afford a wide variety of suture and needle combinations. For example, the channel can have a width of more than about 0.1 inches and less than about 0.7 inches, more preferably about 0.15 inches, and a length of more than about 0.2 and less than about 1.5 inches, more preferably about 0.65 inches. Alternatively, the passageway may comprise a hole or other void such as those shown and described in U.S. Provisional Application Ser. No. 60/405,139, filed Aug. 22, 2002.

Referring to FIG. 12, the jaws 60 are preferably associated with the legs 43 and 45 of the synthetic material 42 by a suture 17, 17A that connects a tine 28 to a leg portion 43 or 45. This may preferably be accomplished with a through hole 9 in tine 28.

Alternatively, the implant assembly tool 20 may be associated with the synthetic material by interaction between a structured surface on the inner surface of jaws 60 and the synthetic material 43 or 45. For example, the structured surface may comprise hooks for a hook and loop type association between the implant assembly tool and the synthetic material. Many different hook and loop type fasteners are believed suitable for use in the present invention, such as the fasteners described in U.S. Pat. No. 3,359,980 to Rosenblatt, U.S. Pat. No. 3,694,867 to Stumpf, U.S. Pat. No. 3,913,183 to Brumlik, U.S. Pat. No. 4,609,581 to Ott, U.S. Pat. No. 4,739,635 to Conley et al., U.S. Pat. No. 4,761,318 to Ott et al. and U.S. Pat. No. 4,770,917 to Tochacek et al. It is also believed that the fasteners described in U.S. Pat. No. 3,192,589 to Pearson, U.S. Pat. No. 3,353,663 to Kayser et al., U.S. Pat. No. 3,408,705 to Kayser et al., U.S. Pat. No. 4,959,265 to Wood et al., U.S. Pat. No. 5,077,870 to Melbye et al., and U.S. Pat. No. 5,196,266 to Lu et al., and EPO published application no. 382 420 to Lu et al. may also be used in accordance with the present invention. The particular structured surface chosen should be sufficiently blunt to avoid damaging surrounding tissue. It should also be sized and shaped to resist harboring microorganisms.

Figure 9:
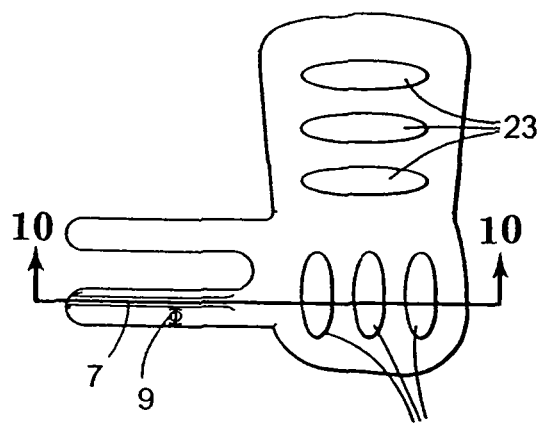
FIG. 9 is a bottom view of a component of the implant assembly tool of FIG. 6.
Figure 11:
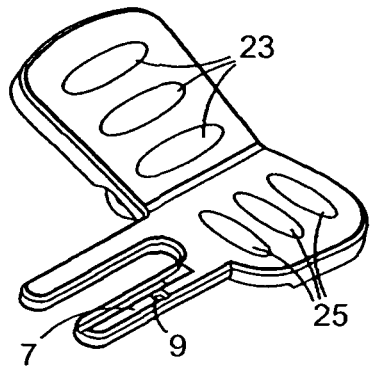
FIG. 11 is a perspective view of the component of FIG. 9.
Figure 10:
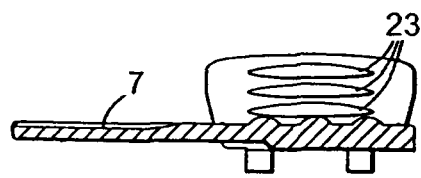
FIG. 10 is a sectional view taken approximately along lines 10-10 of FIG. 9.

As seen in FIGS. 7, 9 and 10, tine 28 of each jaw 60 includes a cutting slot 7 adapted to receive a blade 71 (FIG. 21) to guide the blade 71 as it cuts the suture 17 that associates the tine 28 with a leg portion 43 or 45 to separate the implant assembly tool 20 from the synthetic material 42 once the synthetic material 42 is attached to the biomaterial 50. Indicia 69 is preferably provided to assist the surgeon in visualizing the slot 7. For example, if the material of the tool is a substantially light color, the indicia 69 may be dark. Preferably, the suture that associates the tine with a leg portion includes a pair of knots and/or loops 17 and 17A so that when the suture 17 is cut, the suture remains with the implant assembly tool 20 by virtue of loop or knot 17A. This helps ensure that a portion of suture 17 or 17A is not inadvertently left with the material 42.

As seen in FIG. 7, the jaws 60 include indicia 63 for indicating preferred location of suture passage for attaching the synthetic material 42 to the biomaterial 50. The indicia 63 may comprise bar defining an imaginary area B for preferred passage of the needle/suture combination 99. The indicia 63 may also cooperate with indicia 69 to assist the surgeon in visualizing channel 5.

The jaws 60 preferably include manually engageable portions 29 (FIG. 7) for grasping the assembly tool 20 while the suture and needle combination 99 (See FIGS. 18-20) is passed through the channel 5. This can contribute to the aseptic nature of the composite sling assembly as the surgeon need not touch either biomaterial 50 or either leg 43 or 45.

Referring to FIG. 8, assembly tool 20 also preferably includes biasing means (e.g. a coil spring 2) for biasing the jaws toward the closed position, and opening flanges 22 for pressing on to move the jaws 60 from the closed toward the open position against the bias of the spring 2. Alternative, embodiments of the biasing means are within the scope of the present invention, such as leaf springs, integral springs and the like.

The implant assembly tool 20 includes handle portions 22 and 24 with structure e.g. raised ribs 23 for enhancing manual grasping of the implant assembly tool 20. Jaws 60 may also include similar structures 25 on surface 29 to assist in holding the tool 20 during suturing of the materials 42 and 50.

A variety of different materials may be used to construct assembly tool. Suitable materials are biocompatible and include metals and plastics. Examples of metals include titanium and stainless steels. Suitable polymerics include nylons (e.g. 30% glass filled Nylon), polyethylene, polypropylene and Teflon (e.g. polytetrafluoroethylene), and combinations thereof.

A surgical kit 100 according to the present invention may optionally include additional accessories. For example, a surgical drape specifically designed for urological procedures such as a sling procedure may be included in a kit of the present invention. Such a drape is disclosed in published U.S. Pat. Appl. No. 2002-078964-A1. Alternatively, an article for objectively setting tension of the sling, such as one of the articles described in published U.S. patent application Ser. No. 09/968,239, filed Oct. 1, 2001 may be included in the kit.

The kits 100 according to the present invention optionally include at least two needles. In various embodiments of the present invention, the needles may comprise the needles disclosed in U.S. patent application Ser. No. 10/274,524, filed Oct. 17, 2002, and/or the needles described in published U.S. Pat. Application Nos. 2002-0151762-A1; 2002-0147382-A1; 2002-0107430-A1, US-2002-0099258-A1 and US-2002-0099259-A1; and U.S. Provisional Application Ser. Nos. 60/263,472, filed Jan. 23, 2001; 60/269,829, filed Feb. 20, 2001; 60/281,350, filed Apr. 4, 2001; 60/295,068, filed Jun. 1, 2001; 60/306,915, filed Jul. 20, 2001, and U.S. Provisional Patent Application No. 60/332,330, filed Nov. 20, 2001. In an embodiment that is particularly suitable for a transobturator surgical procedure, the needles comprise needles as described in U.S. patent application Ser. No. 10/306,179 filed Nov. 27, 2002.

In some instances the needles may be substantially identical, in other instances, they may be different. Two or more needles reduce the need to reuse a non-sterile needle at a different location with a patient, thereby eliminating cross contamination issues. Additional needles, handles, dilators and other elements may also be included for surgical convenience, for avoidance of contamination from one portion of the body to another, for ease of manufacturing or sterilization or for surgical requirements.

A composite sling assembly may be assembled by the surgeon or provided preassembled using the teachings or components of published U.S. Pat. Application Nos. 2002-0147382-A1 or 2002-0082619-A1. The individual elements of the kits of the present invention may be packaged together as shown in FIG. 14, separately or in subassemblies depending on a variety of factors such as shelf life and sterilization requirements. They may be assembled at the manufacturing location or at the healthcare location. Any suitable sterilization procedure may be utilized to sterilize the contents of a kit. Suitable sterilization techniques include, but are not limited to steam, ethylene oxide, electron beam, vapor (e.g. hydrogen peroxide or peracetic acid), gamma or plasma procedures. For example, the needles 16 may be reusable or single use devices. FIG. 14 illustrates an embodiment with a composite sling assembly may be assembled by the surgeon or provided preassembled using the teachings or components of published U.S. Pat. Application Nos. 2002-0147382-A1 or 2002-0082619-A1. The individual elements of the kits of the present invention may be packaged together as shown in FIG. 14, separately or in subassemblies depending on a variety of factors such as shelf life and sterilization requirements. They may be assembled at the manufacturing location or at the healthcare location. Any suitable sterilization procedure may be utilized to sterilize the contents of a kit. Suitable sterilization techniques include, but are not limited to steam, ethylene oxide, electron beam, vapor (e.g. hydrogen peroxide or peracetic acid), gamma or plasma procedures. For example, the needles 16 may be reusable or single use devices. FIG. 14 illustrates an embodiment with two needles 16 and two subassemblies 10 (e.g. see FIG. 1) with typical packaging such as a tray T, inserts I and covers C. These components may have relatively similar shelf lives (as opposed to some biomaterials) and are thus preferably packaged together. A biomaterial (e.g. adaveric fascia) 50 for forming a mid-portion of a sling would preferably be packaged separately as it is likely to have a substantially different shelf life.

The above-described surgical instruments may be disposable or reusable. Optionally, portions of the surgical instrument may be reusable (sterilizable) and other components may be disposable.

EXAMPLES OF SURGICAL PROCEDURES

Several methods are contemplated herein. Although the methods of use as disclosed herein generally relate to female incontinence conditions and treatments/procedures, male incontinence conditions and treatments/procedures are also included within the scope of the present invention. The present invention may also be utilized to correct other pelvic floor defects concomitantly or as a dedicated article or procedure. Examples of particular applications include, but are not limited to vault prolapse repair, paravaginal defect repairs, and repairs of cystoceles, rectoceles, and enteroceles. Further, the term "urethra," with respect to sling positioning, is used for brevity and reader convenience.

The present invention is particularly suitable for placing a sling in a therapeutically effective position. The method may be utilized to support a variety of structures at different anatomical locations. Variations of these methods may occur due to individual surgeon's techniques or a patient's particular anatomy.

Referring to FIGS. 15 through 23, there is shown a method for assembling a composite sling for use in a sling procedure similar to that provided in the instructions for use in the SPARC Sling System, available from American Medical Systems of Minnetonka, Minn. However, it is noted that the present invention may be utilized in alternative surgical approaches and anchoring methods such as those described in the instructions for use for the TVT procedure, the In-Fast Ultra surgical procedure available from American Medical Systems of Minnetonka, Minn., and the procedures described in U.S. Pat. Nos. 5,899,909; 6,406,480, published U.S. Pat. Application Nos. 2002/0188169 A1 and 2002/0022841 A1, and U.S. patent application Ser. No. 10/106,086, filed Mar. 25, 2002, and U.S. patent application Ser. No. 10/306,179 filed Nov. 27, 2002.

For a transobturator procedure, the present invention may comprise a surgical method for treating incontinence, comprising the steps of: (1) providing a first sling segment comprising a synthetic material having a distal end and an attachment end; and a second sling segment comprising a synthetic material having a distal end and an attachment end; (2) integrating a biomaterial with the attachment ends of the first and second segments so that the biomaterial may be placed underneath the patient's urethra, and (3) then implanting the first and second segments and the integrated biomaterial so that they provide a sling extending from a position substantially adjacent the patient's obturator foramen in the pelvic region, to a position below the patient's urethra, and then to the patient's obturator foramen on an opposite side of the patient's urethra.

Returning to FIGS. 15 through 23, the present invention will be described with reference to a surgical procedures that initially introduces needles through the abdominal wall and then passes them out a vaginal incision. These figures show subassemblies 10 of FIGS. 1 through 3 being used to construct a composite sling.

The surgeon selects and prepares (if required) the desired graft or biologic material 50. For example, the graft material may comprise InteXen, InteDerm or InteLata graft materials available from American Medical Systems, of Minnetonka, Minn. Some graft materials may be folded to increase attachment strength to the Y-shaped portion of the mesh. Some examples may be found in the table below:

| Type | Attachment Recommendation |
| --- | --- |
| InteXen | No Fold |
| InteDerm | No Fold |
| InteLata | Folded Ends |
| Autologus | Folded Ends |

Figure 15:
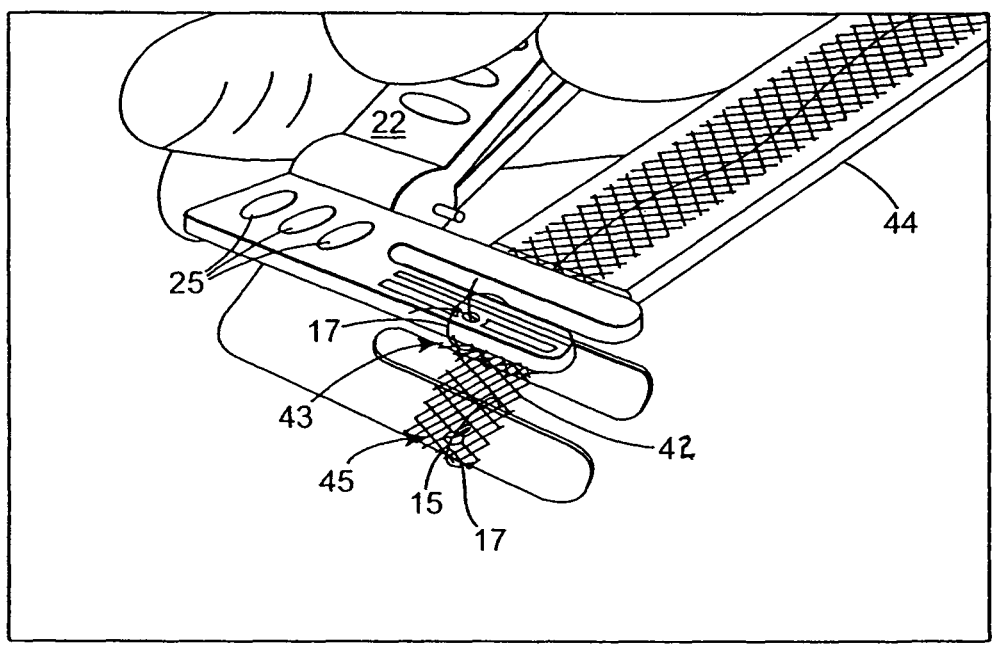
FIG. 15 is a schematic view of an implant assembly tool and synthetic implant material in an open position.
Figure 16:
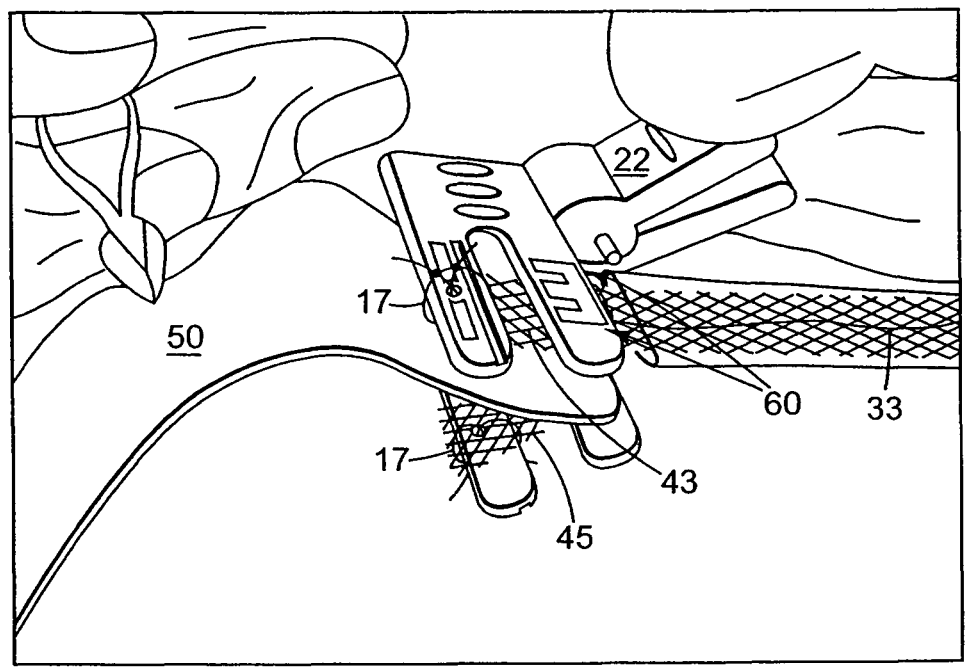
FIG. 16 is a schematic view of the implant assembly tool and implant of FIG. 15 and a biological material inserted between portions of the synthetic implant material.
Figure 17:
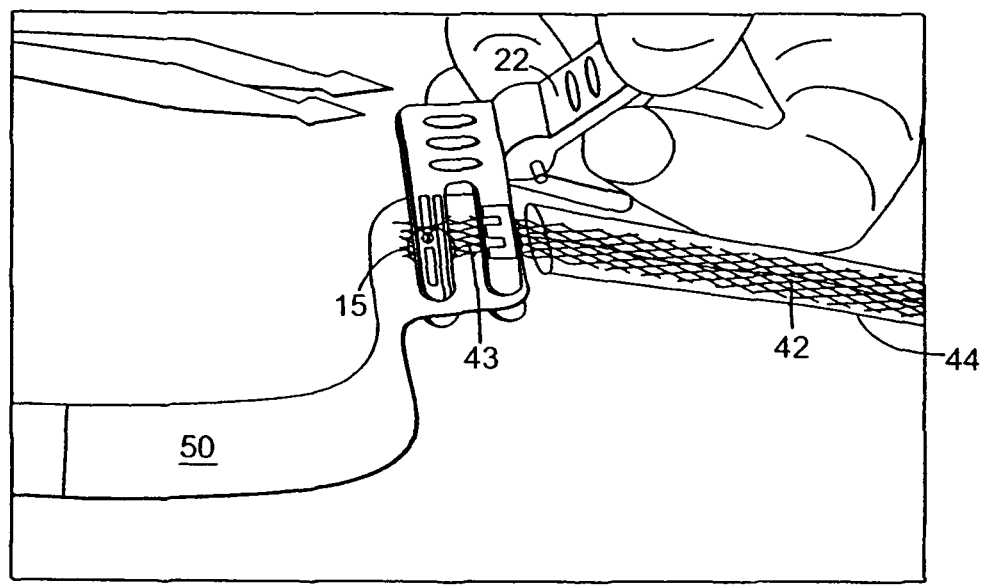
FIG. 17 is a schematic view of the components of FIG. 16 after the implant assembly tool is released and allowed to move from the open toward its closed position.

Referring to FIG. 15, handles 22 and 24 are squeezed to open the tool 20. In FIG. 16, the surgeon's choice of graft material is aseptically inserted into the Y-mesh, preferably using printed marks 63 (FIG. 7) on the tool 20 as guides to center the graft. In FIG. 17, the surgeon releases handles 22 and 24 to close the tool 20 to secure the graft material between the legs 43 and 45 of the Y-shaped portion.

Figure 18:
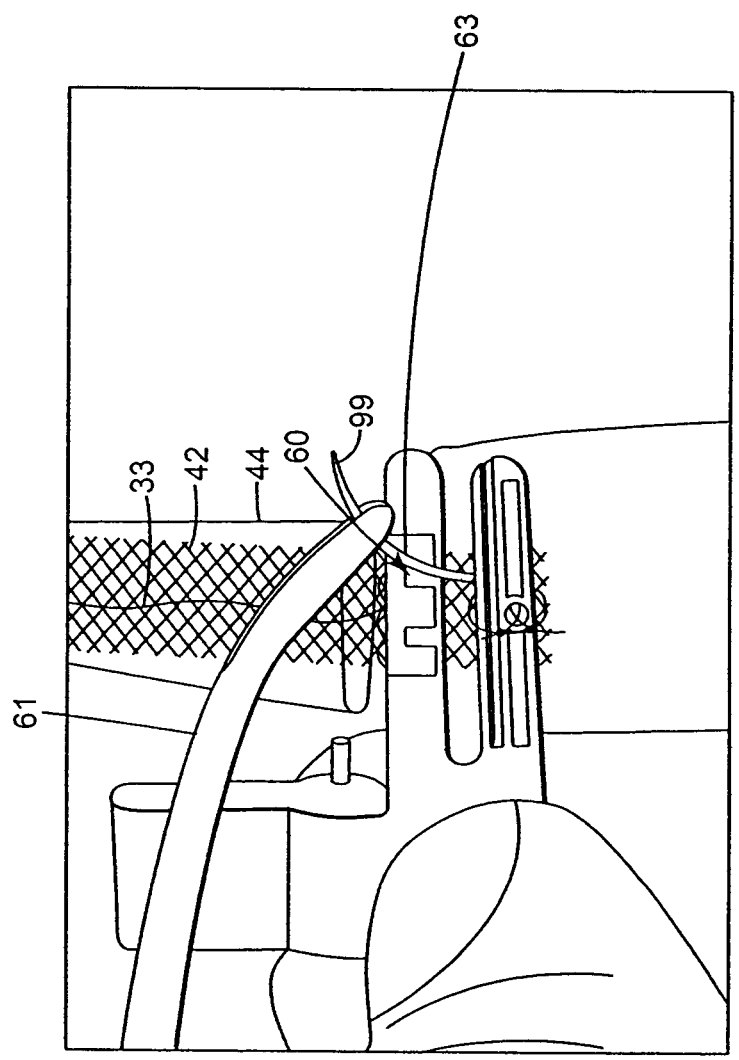
FIG. 18 is a schematic view showing a suture being threaded through the synthetic and biological materials by passing a needle through a channel in the implant assembly tool with the needle being grasped by a surgical clamp.
Figure 19:
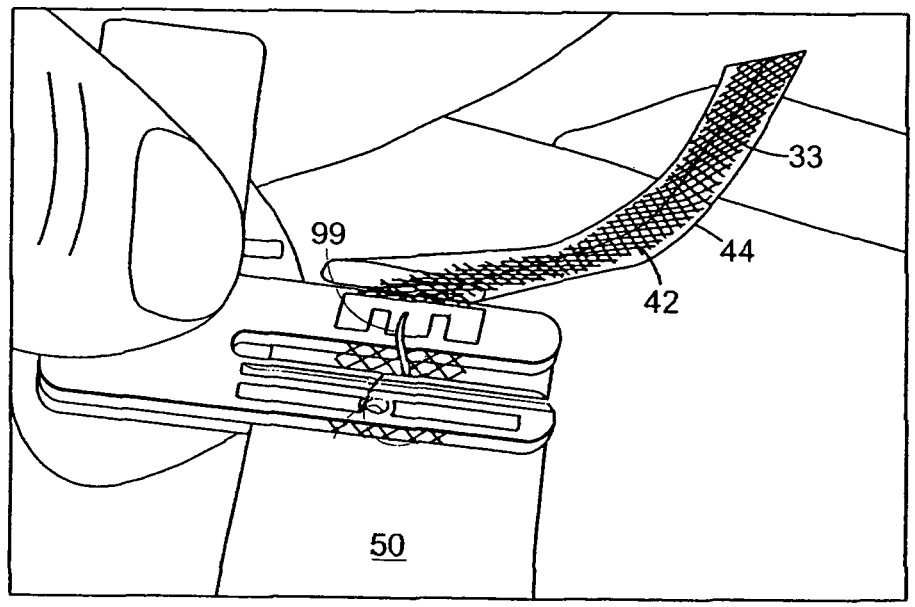
FIG. 19 is a schematic view showing a suture being threaded through the synthetic and biological materials by passing a needle through a channel in the implant assembly tool similar to FIG. 18 but just prior to the needle being grasped by a surgical clamp.

Using the surgeon's choice of suture/needle combination, a suture is passed up using a suture/needle combination 99. A clamp 61 (e.g. a hemostat) may contribute to the aseptic nature of the suture passage (FIG. 18). FIG. 19 shows the needle 99 prior to being grasped by the clamp 61. The suture mark 63 may be used as a guide for passage of the suture. Preferably, the sutures are passed in the area defined by imaginary box B shown in FIG. 7. The sutures are preferably passed so that the attachment knots are on an optional printed side of the sheath 44 in order, for example, to control the final orientation of the knots relative to the urethra. The suture is then passed down using the opposite suturing mark (see 63) as a guide.

Figure 20A:
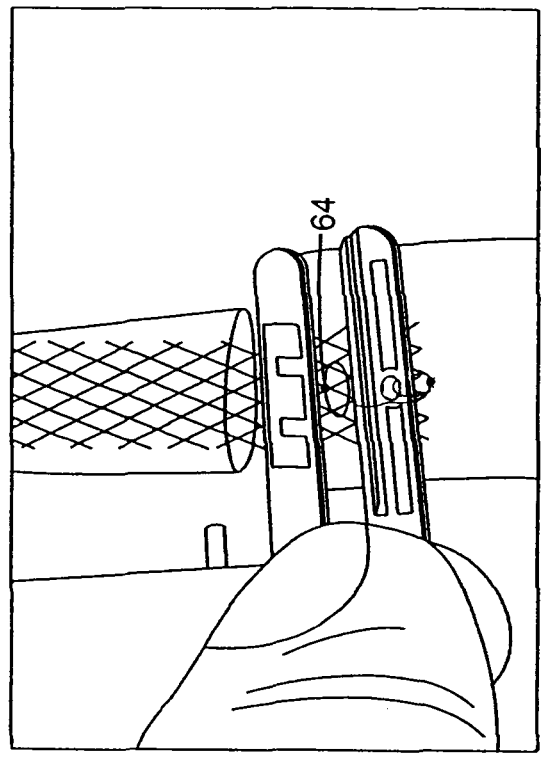
FIG. 20A shows the suture of FIG. 20 just after it is tied.
Figure 20:
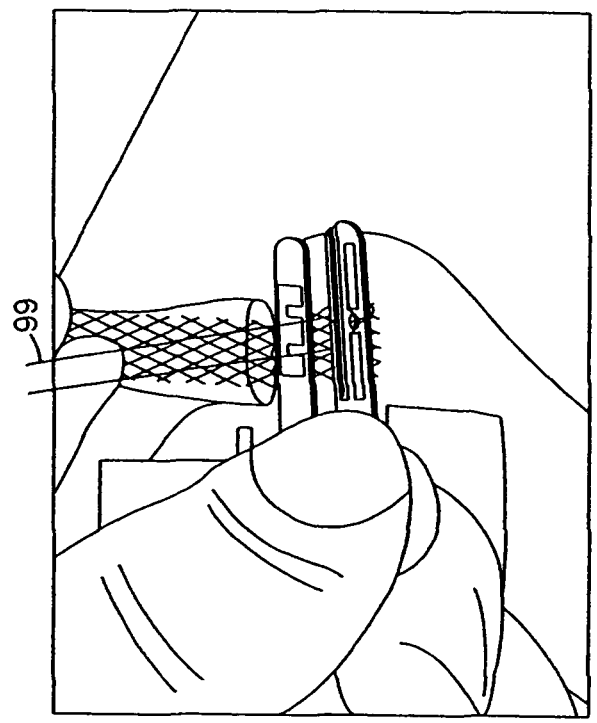
FIG. 20 is a schematic view showing a suture after it is passed through the implant and just prior to being tied.

Referring to FIGS. 20 and 20A, the passed suture 99 is then secured using a knot 64 of the surgeon's choice (e.g. a surgeon's knot). Suitable knots for use in this and other embodiments of the present invention are described in the ETHICON Knot Tying Manual (©1999-2000), available from ETHICON, of NJ. Additional knots and/or throws may be accomplished if desired or needed. For example, when using InteLata from American Medical Systems (Human Fascia Lata), two suture throws may be preferred.

Figure 21:
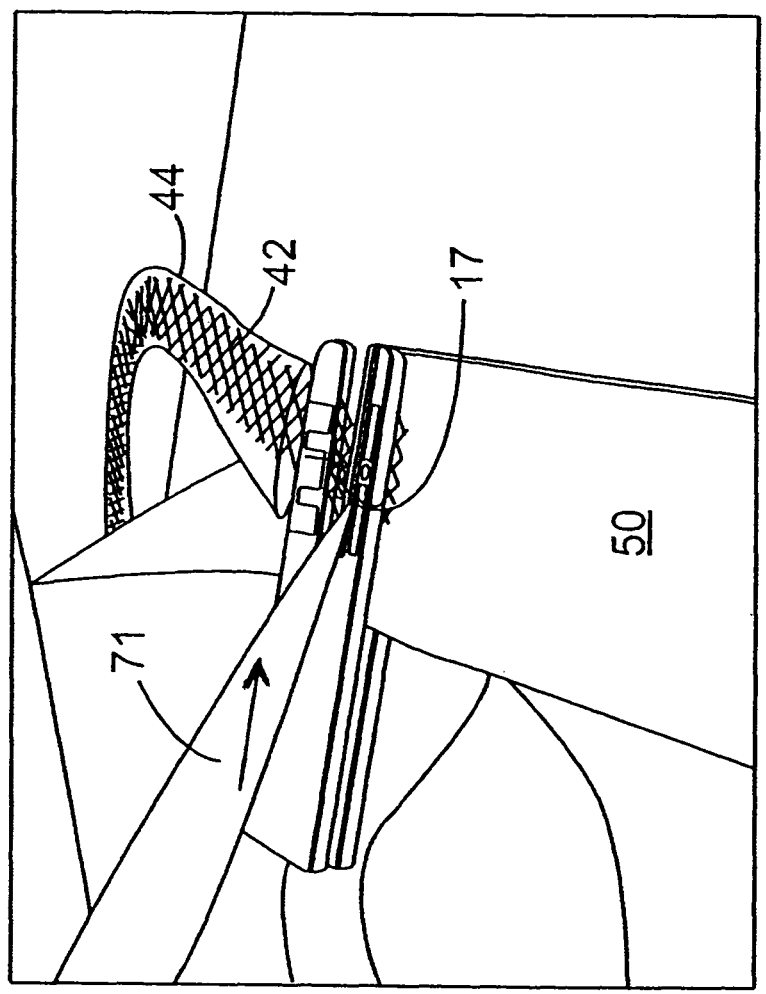
FIG. 21 is a schematic view of a blade being drawing along a slot in the implant assembly tool to cut a suture that holds the implant assembly tool to the synthetic implant material.

Referring to FIG. 21, a blade 71 (e.g. knife, scalpel or scissors) is then utilized to cut assembly tool sutures 17 by passing the blade 71 down groove 7 in each jaw 60 of the tool 20. A suture is cut on each side of the mesh 42. Preferably, the direction of cutting is away from the surgeon. Optional printing 69 helps indicate the location of the groove 7. The implant assembly tool 20 may then be removed from the assembled implant 42/50. Notably, the tool sutures 17 remain with the assembly tool 20 due to the second knot 17A (see FIG. 12).

Next, the steps are repeated on the opposite side of the biologic material 50 using another subassembly 10.

Initially, the patient is placed under local, spinal or general anesthesia. A catheter (e.g. Foley) may be inserted through the urethra. Two small transverse suprapubic abdominal stab incisions may be made near the back of the pubic bone (e.g. each about 1 cm from the midline, or alternatively, one large incision may be made) to allow for needle entry. A small incision (e.g. a transverse incision) is made in the anterior vaginal wall followed by a transurethral dissection. For example, a 1.5 cm vertical incision on the anterior vaginal wall starting approximately 1.0 cm from the urethral meatus may be performed. Two small paraurethral dissections may be made to allow the surgeon finger to meet blunt distal end 58 of needle 16. The amount of dissection may vary according to surgeon preference.

Needles 16 may be inserted by initially passing distal ends 58 through abdominal incisions and then through a vaginal incision. The dilators 54 may then be connected to the distal end 58 of the needle emerging from the vaginal incision.

If printing on the sheath 44 is utilized, the printed side of the sheath is placed away from the urethra, facing the surgeon. One dilator 54 is attached to each of the needles on the ends 58. The surgeon then inspects the assembly to ensure that the sling is substantially flat (not canoe shaped or twisted prior to attaching the second dilator 54 to the second needle 16).

Once the needles 16 are securely attached to the dilators 54, the needles 16 are pulled up through the suprapubic (abdominal) incision(s).

When positioning the sling into place; the surgeon ensures that the biologic material of choice is generally flat under the urethra, which may facilitate healing in the immediate postoperative period. This may be accomplished by the method preferred by the physician; such as trimming, providing lateral dissection to allow the material to lay flat against the urethra, or suturing the biologic of choice on either side of the urethra (e.g. at four points).

Each end of the sling mesh projecting from the abdominal incision(s) may be secured with a hemostat or a clamp. The sling mesh may be cut approximately 3 cm away from the dilating connectors 54, assuring that the surgeon has cut below the optional markings at each end of the sheath 44.

The sling is preferably positioned under the midurethra without tension. Preferably the biological material 50 is centered under the urethra keeping suture knots away from the urethra prior to removing the sheaths 44.

After desired placement is achieved, the surgeon removes the sheath 44 from the sling mesh 42 by pulling up from both sides, preferably one side at a time. To avoid over-tightening the sling while removing the sheath 44, a surgeon may keep a forceps or other instrument between the graft material 50 and urethra during removal.

The tensioning suture 33 in the sling mesh may be used for further tensioning adjustment once the sheath 44 is removed. The tensioning suture 33 allows for adjustment of the sling mesh in the immediate post-operative period.

To tighten the sling, the surgeon may place a device such as a clamp, across the mesh 42, suprapubically. Preferably, the surgeon ensures that both the tensioning suture 33 and the complete width of the sling mesh 42 are captured within the clamp. The sling mesh may then be rolled around the clamp to improve the grip. The surgeon pulls up to tighten the sling mesh as desired. If needed, this can be repeated on the contralateral side.

Figure 23:
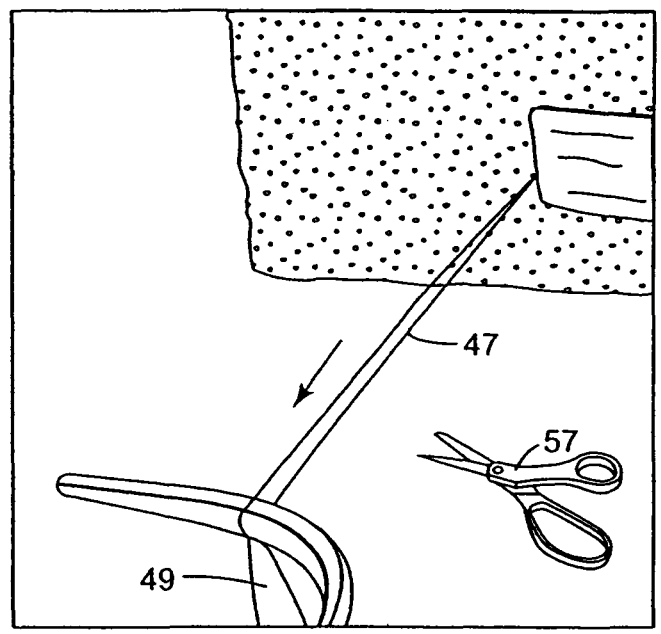
FIG. 23 shows a loosening loop being pulled to loosen the tension of an implanted sling.

Referring to FIG. 23, to loosen the composite implant, the surgeon may use a hemostat or a clamp 49 to pull from one or more of the hanging loosening loops 47 (only one is shown in FIG. 23). The clamp 49 is used to pull down and loosen the composite sling as desired. The loosening loops 47 are then cut (e.g. with scissors 57) and tab 49 may be pulled on to release loop 47. Because the loop 47 includes two knots 76, 78 (FIG. 13), the loop 47 may be released without passing a knot through the mesh 42.

The precise, final location of the composite sling will depend on a variety of factors including the particular surgical procedure(s) performed, and any preconditions of the patient such as scar tissue or previous surgeries. For example, it may be preferred to place the portion 50 of the sling in close proximity to, but not in contact with, a mid portion of the urethra to treat incontinence. Alternatively, the sling may be placed near the bladder neck.

When the surgeon is satisfied with the final placement, the distal ends of the sling mesh 42 are again trimmed to size at the suprapubic incisions, and the suprapubic and vaginal incisions are closed. At the surgeon's discretion, a Foley catheter or suprapubic tube can be utilized until the patient is able to void.

All patents, patent applications, product instructions for use, conference proceedings and publications cited herein are hereby incorporated by reference in their entirety as if individually incorporated.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical method for treating a pelvic floor disorder, comprising:

providing a sling having first and second ends to define a sling length, an intermediate portion adapted to support the urethra or the bladder neck, a translucent sheath covering at least a portion of the first end and the second end, and a continuous tensioning suture having a suture length adapted to contiguously extend from the first end, to the intermediate portion and to the second end to extend substantially along the entire longitudinal length of the sling, with the continuous tensioning suture interlaced with the sling, including interlaced through a plurality of mesh filaments substantially at a midpoint juncture of the longitudinal length of the sling and the suture length of the continuous tensioning suture, to provide an undulation along the longitudinal length of the sling such that an end of the suture extends out from the sheath at the second end of the sling, and the sheath includes one or more position markings;

providing a delivery device having a distal portion adapted for releasable attachment to the first end or second end of the sling;

attaching the distal portion of the delivery device to the first end of the sling;

delivering the first end of the sling to a therapeutically effective location in the pelvic region of a patient;

fixing the first end of the sling into the tissue of the patient;

detaching the delivery device from the first end of the sling;

attaching the distal portion of the delivery device to the second end of the sling;

delivering the second end of the sling to a therapeutically effective location in the pelvic region of the patient, the location being generally contralateral to the fixated location of the first end of the sling;

fixing the second end of the sling into the tissue of the patient;

removing the sheath; and clamping across a width of the sling with a clamp tool such that a length of the tensioning suture and the width of the sling are secured in the clamp tool, the clamp tool including a slot adapted to guide a blade for cutting suture.

2. The method of claim 1, wherein providing the sling includes providing the sling constructed of a porous mesh material.

3. The method of claim 1, wherein providing the continuous tensioning suture includes providing the continuous tensioning suture generally midway between the longitudinal edges of the sling.

4. The method of claim 1, wherein providing the sling includes providing a generally elongate sling.

5. The method of claim 1, wherein providing the sling includes providing the sling having a y-shaped portion at least at one of the first or second ends.

6. The method of claim 1, further including creating a single vaginal incision to facilitate introduction of the distal portion of the delivery device and the sling.

7. The method of claim 1, further including creating a single vaginal incision, and at least one skin incision to facilitate introduction of at least the distal portion of the delivery device.

8. The method of claim 1, further including fixing at least one of the first or second ends to the obturator foramen of the patient.

9. The method of claim 1, further including fixing at least one of the first or second ends in the retropubic space of the patient.

10. The method of claim 1, wherein at least one of the first and second ends includes an anchor.

11. The method of claim 1, wherein the first and second ends include an anchor.

12. The method of claim 1, wherein the continuous tensioning suture is affixed to the first end of the sling via a weld.

13. The method of claim 1, wherein the continuous tensioning suture is affixed to the first end of the sling via a knot.

14. The method of claim 1, wherein the continuous tensioning suture is affixed to the first end of the sling via an adhesive.

* * * * *